(12) United States Patent
Ouyang et al.

(10) Patent No.: US 12,220,235 B2
(45) Date of Patent: Feb. 11, 2025

(54) ANALYTE SENSORS AND SENSING METHODS FOR DUAL DETECTION OF GLUCOSE AND ETHANOL

(71) Applicant: Abbott Diabetes Care Inc., Alameda, CA (US)

(72) Inventors: Tianmei Ouyang, Fremont, CA (US); Benjamin J. Feldman, Berkeley, CA (US); Hyun Cho, Berkeley, CA (US); Lam N. Tran, Dublin, CA (US); Stephen Oja, Alameda, CA (US); Namvar Kiaie, San Jose, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 431 days.

(21) Appl. No.: 16/774,909

(22) Filed: Jan. 28, 2020

(65) Prior Publication Data

US 2020/0237277 A1    Jul. 30, 2020

Related U.S. Application Data

(60) Provisional application No. 62/884,841, filed on Aug. 9, 2019, provisional application No. 62/797,566, filed on Jan. 28, 2019.

(51) Int. Cl.
*A61B 5/1486* (2006.01)
*A61B 5/00* (2006.01)
(Continued)

(52) U.S. Cl.
CPC ...... *A61B 5/14865* (2013.01); *A61B 5/14532* (2013.01); *A61B 5/4845* (2013.01);
(Continued)

(58) Field of Classification Search
CPC ............ A61B 5/14865; A61B 5/14532; A61B 5/1451; A61B 5/14546; A61B 5/4845;
(Continued)

(56) References Cited

U.S. PATENT DOCUMENTS 5,264,105 A   11/1993   Gregg et al.
5,696,314 A   12/1997   McCaffrey et al.
(Continued)

FOREIGN PATENT DOCUMENTS

CN   101849180 B   8/2017
JP   2007290504 A   11/2007
(Continued)

OTHER PUBLICATIONS

D'Allegro, Joe. "Soon Your Car Will Know When You Are Having a Heart Attack—and Know How to React." CNBC, Nov. 17, 2017, www.cnbc.com/2017/11/17/cars-will-know-when-youre-having-a-heart-attack-and-how-to-react.html. Accessed Jul. 29, 2023. (Year: 2017).*

(Continued)

*Primary Examiner* — Puya Agahi
*Assistant Examiner* — Alice Ling Zou
(74) *Attorney, Agent, or Firm* — Sterne, Kessler, Goldstein & Fox P.L.L.C.

(57) ABSTRACT

Multiple enzymes may be present in one or more active areas of an electrochemical analyte sensor for detecting one or more different analytes. In particular, an analyte sensor may comprise a sensor tail configured for insertion into a tissue and one or more working electrodes having a glucose-responsive active area and an ethanol-responsive active area to detect glucose and ethanol in vivo.

12 Claims, 10 Drawing Sheets

(51) Int. Cl.
*A61B 5/145* (2006.01)
*B60K 28/06* (2006.01)
*C12Q 1/30* (2006.01)
*C12Q 1/32* (2006.01)

(52) U.S. Cl.
CPC .............. *B60K 28/06* (2013.01); *C12Q 1/30* (2013.01); *C12Q 1/32* (2013.01); *B60K 28/063* (2013.01); *B60K 28/066* (2013.01)

(58) Field of Classification Search
CPC . C12Q 1/30; C12Q 1/32; C12Q 1/006; C12Q 1/001–005; C12Q 2/16; C12Q 2521/543; G01N 33/98; G01N 2333/90203; G01N 2333/90209; G01N 2333/904; G01N 2333/908
See application file for complete search history.

(56) References Cited

U.S. PATENT DOCUMENTS

| | | | |
|---|---|---|---|
| 5,792,621 | A | 8/1998 | Verostko |
| 6,127,138 | A * | 10/2000 | Ishimaru ................ C12N 9/62 435/23 |
| 6,134,461 | A | 10/2000 | Say et al. |
| 6,241,863 | B1 | 6/2001 | Monbouquette |
| 6,605,200 | B1 | 8/2003 | Mao et al. |
| 6,605,201 | B1 | 8/2003 | Mao et al. |
| 6,736,957 | B1 | 5/2004 | Forrow |
| 7,501,053 | B2 | 3/2009 | Karinka et al. |
| 7,563,588 | B2 | 7/2009 | Gao et al. |
| 7,754,093 | B2 | 7/2010 | Forrow et al. |
| 8,268,143 | B2 | 9/2012 | Liu et al. |
| 8,444,834 | B2 | 5/2013 | Liu et al. |
| 8,545,693 | B2 | 10/2013 | McColl et al. |
| 10,136,816 | B2 | 11/2018 | Bernstein et al. |
| 2001/0003045 | A1 | 6/2001 | Davis et al. |
| 2003/0100821 | A1 | 5/2003 | Heller et al. |
| 2006/0004272 | A1 | 1/2006 | Shah |
| 2007/0027385 | A1 | 2/2007 | Brister et al. |
| 2007/0213611 | A1 | 9/2007 | Simpson et al. |
| 2008/0179187 | A1 | 7/2008 | Ouyang et al. |
| 2008/0319295 | A1 | 12/2008 | Bernstein et al. |
| 2009/0294306 | A1 | 12/2009 | Feldman et al. |
| 2010/0116691 | A1 * | 5/2010 | Papadimitrakopoulos ................ G01N 33/6803 204/403.14 |
| 2010/0213057 | A1 | 8/2010 | Feldman et al. |
| 2010/0230285 | A1 | 9/2010 | Hoss et al. |
| 2010/0267161 | A1 | 10/2010 | Wu et al. |
| 2011/0046467 | A1 | 2/2011 | Simpson et al. |
| 2011/0213225 | A1 | 9/2011 | Bernstein et al. |
| 2012/0132525 | A1 | 5/2012 | Liu et al. |
| 2012/0150005 | A1 | 6/2012 | Hoss et al. |
| 2012/0181189 | A1 | 7/2012 | Merchant |
| 2012/0186997 | A1 | 7/2012 | Li et al. |
| 2012/0283537 | A1 | 11/2012 | Petisce et al. |
| 2013/0131478 | A1 | 5/2013 | Simpson et al. |
| 2013/0211219 | A1 | 8/2013 | Coppeta et al. |
| 2013/0324820 | A1 * | 12/2013 | Petillo ................ A61B 5/14865 205/109 |
| 2014/0054171 | A1 * | 2/2014 | Feldman ............ G01N 27/3272 204/403.14 |
| 2014/0127728 | A1 | 5/2014 | Wilsey |
| 2014/0176338 | A1 | 6/2014 | He et al. |
| 2014/0262776 | A1 | 9/2014 | Martin et al. |
| 2014/0262777 | A1 | 9/2014 | Zhao et al. |
| 2015/0207796 | A1 | 7/2015 | Love et al. |
| 2016/0319232 | A1 * | 11/2016 | Noritomi ................ C12M 21/18 |
| 2017/0156652 | A1 | 6/2017 | Qiang |
| 2017/0315077 | A1 | 11/2017 | Rao et al. |
| 2018/0116604 | A1 * | 5/2018 | Newberry ............ A61B 5/4845 |
| 2019/0004005 | A1 | 1/2019 | Oja et al. |
| 2019/0271658 | A1 | 9/2019 | Haneda et al. |
| 2019/0274598 | A1 | 9/2019 | Scott et al. |
| 2020/0069226 | A1 | 3/2020 | Hahn et al. |
| 2020/0237275 | A1 | 7/2020 | Feldman et al. |
| 2020/0237276 | A1 | 7/2020 | Oja et al. |
| 2020/0241015 | A1 | 7/2020 | Ouyang et al. |
| 2021/0137431 | A1 | 5/2021 | Oja et al. |
| 2021/0254120 | A1 * | 8/2021 | Plumeré ................ C12Q 1/30 |
| 2022/0168727 | A1 | 6/2022 | Baldwa |
| 2023/0118818 | A1 | 4/2023 | Feldman et al. |
| 2023/0119512 | A1 | 4/2023 | Feldman et al. |
| 2023/0121101 | A1 | 4/2023 | Feldman et al. |
| 2023/0121367 | A1 | 4/2023 | Feldman et al. |
| 2023/0121769 | A1 | 4/2023 | Feldman et al. |
| 2023/0122702 | A1 | 4/2023 | Feldman et al. |
| 2023/0123384 | A1 | 4/2023 | Feldman et al. |
| 2023/0128038 | A1 | 4/2023 | Feldman et al. |

FOREIGN PATENT DOCUMENTS

| | | |
|---|---|---|
| JP | 2010517054 A | 5/2010 |
| JP | 2010530790 A | 9/2010 |
| JP | 2013504053 A | 2/2013 |
| JP | 2014503080 A | 2/2014 |
| JP | 2018029983 A | 3/2018 |
| WO | 2005040404 A1 | 5/2005 |
| WO | WO-2009105337 A2 | 8/2009 |
| WO | WO-2011030093 A1 | 3/2011 |

OTHER PUBLICATIONS

Guiseppi-Elie et al, "Design of a Subcutaneous Implantable Biochip for Monitoring of Glucose and Lactate," IEEE Sensors Journal, Jun. 1, 2005.
C.S. Pundir et al, "Biosensing Methods for Determination of Creatinine: A Review," Biosensors and Bioelectronics Journal, Nov. 19, 2018.
ISR/WO for PCT/US2020/015400 related to the present application and dated Apr. 9, 2020.
Cardosi, M., et al., "Amperometric Glucose Sensors for Whole Blood Measurement Based on Dehydrogenase Enzymes," in *Dehydrogenases*, Chapter 13, pp. 319-354, InTech, United Kingdom (2012).
Office Action mailed Sep. 17, 2021, in U.S. Appl. No. 16/774,835, Feldman, B., et al., filed Jan. 28, 2020, 21 pages.
Office Action mailed Apr. 18, 2022, in U.S. Appl. No. 16/774,835, Feldman, B., et al., filed Jan. 28, 2020, 24 pages.
Office Action mailed Jun. 23, 2022, in U.S. Appl. No. 16/774,841, Oja, S., et al., filed Jan. 28, 2020, 10 pages.
Office Action mailed Sep. 1, 2022, in U.S. Appl. No. 16/582,583, Ouyang, T., et al., filed Sep. 25, 2019, 20 pages.
Office Action mailed Nov. 16, 2022, in U.S. Appl. No. 16/774,841, Oja, S., et al., filed Jan. 28, 2020, 10 pages.
Office Action mailed Nov. 25, 2022, in U.S. Appl. No. 17/151,274, Oja, S., et al., filed Jan. 18, 2021, 13 pages.
Office Action mailed Mar. 2, 2023, in U.S. Appl. No. 16/774,835, Feldman, B., et al., filed Jan. 28, 2020, 14 pages.
Shi, G., et al., "The study of Nafion/xanthine oxidase/Au colloid chemically modified biosensor and its application in the determination of hypoxanthine in myocardial cells in vivo," Analyst 127(3):396-400, The Royal Society of Chemistry, United Kingdom (Mar. 2002).
Mueller, S., et al., "The GOX/CAT system: A novel enzymatic method to independently control hydrogen peroxide and hypoxia in cell culture," Adv Med Sci 54(2):121-35, Medical University of Bialystok, Poland (2009).
Burmeister, J., et al., "Self-referencing ceramic-based multisite microelectrodes for the detection and elimination of interferences from the measurement of L-glutamate and other analytes," Anal Chem 73(5):1037-42, American Chemical Society, United States (Mar. 2001).
Monteiro, T., et al., "Construction of effective disposable biosensors for point of care testing of nitrite," Talanta 142:246-51, Elsevier, Netherlands (Sep. 2015).
Final Office Action mailed Apr. 19, 2023, in U.S. Appl. No. 16/582,583, 18 pages.

(56) References Cited

OTHER PUBLICATIONS

Office Action mailed Oct. 3, 2023, in U.S. Appl. No. 16/582,583, 21 pages.
Office Action mailed Sep. 12, 2023, in U.S. Appl. No. 16/774,835, 16 pages.
Notice of Allowance mailed Aug. 16, 2023, in U.S. Appl. No. 16/774,841, 10 pages.
Office Action mailed Sep. 7, 2023, in U.S. Appl. No. 17/151,274, 13 pages.
Office Action mailed Sep. 22, 2023, in U.S. Appl. No. 17/819,099, 24 pages.
Final Office Action mailed May 16, 2024, in U.S. Appl. No. 16/582,583, 21 pages.
Non-Final Office Action mailed Apr. 15, 2024, in U.S. Appl. No. 16/774,835, 16 pages.
Non-Final Office Action mailed Feb. 15, 2024, in U.S. Appl. No. 18/068,072, 13 pages.
Non-Final Office Action mailed Jun. 18, 2024, in U.S. Appl. No. 18/068,704, 14 pages.
Non-Final Office Action mailed Jul. 15, 2024, in U.S. Appl. No. 18/068,860, 13 pages.
Non-Final Office Action mailed Feb. 29, 2024, in U.S. Appl. No. 18/068,019, 12 pages.
Non-Final Office Action mailed Jan. 31, 2024, in U.S. Appl. No. 18/068,834, 10 pages.
Notice of Allowance mailed Feb. 7, 2024, in U.S. Appl. No. 17/151,274, 8 pages.
Non-Final Office Action mailed Mar. 5, 2024, in U.S. Appl. No. 18/068,714, 14 pages.

* cited by examiner

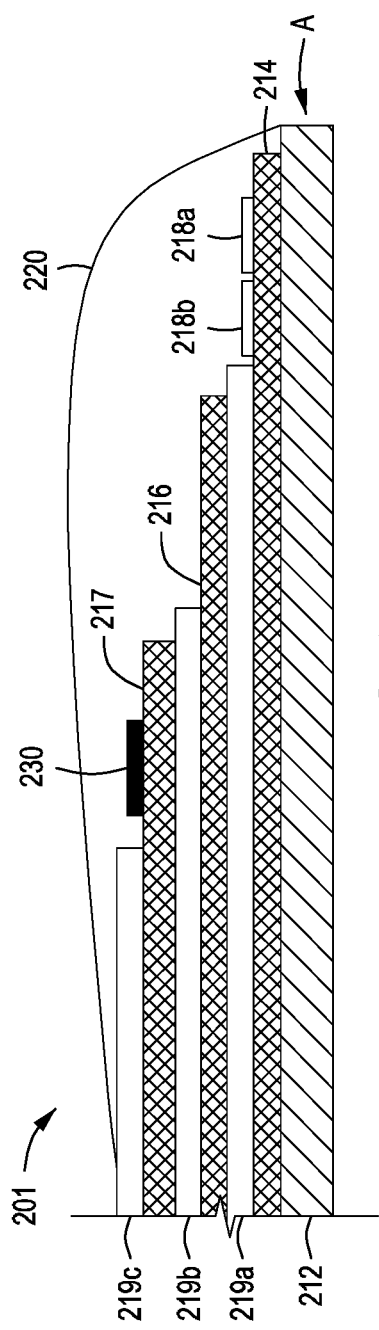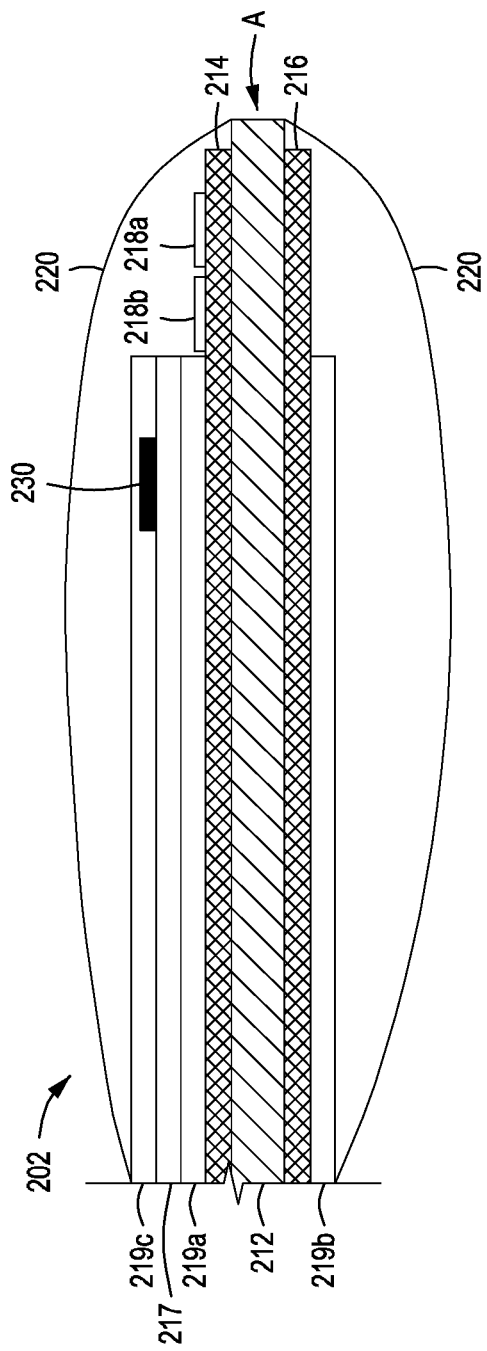

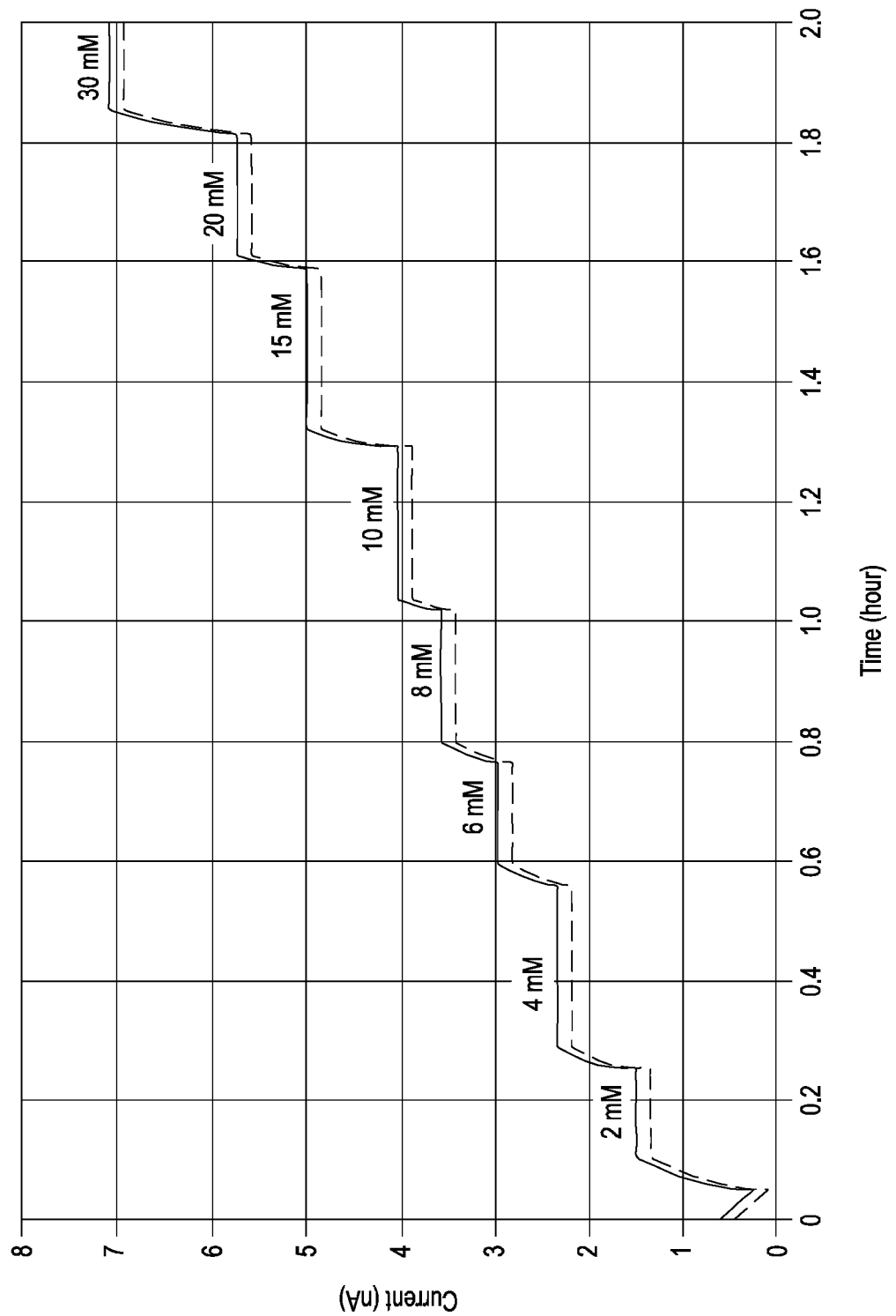

ns, and equivalents in form and function, without
departing from the scope of this disclosure.

ANALYTE SENSORS AND SENSING METHODS FOR DUAL DETECTION OF GLUCOSE AND ETHANOL

CROSS-REFERENCE TO RELATED APPLICATIONS

The present application claims the benefit of priority of U.S. Provisional Application 62/797,566 entitled "Analyte Sensors Employing Multiple Enzymes and Methods Associated Therewith," filed on Jan. 28, 2019, and U.S. Provisional Application 62/884,841 entitled "Analyte Sensors and Sensing Methods for Dual Detection of Glucose and Ethanol," filed on Aug. 9, 2019, the entireties of which is incorporated herein by reference.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental conditions. While a single analyte may be singularly dysregulated for a given physiological condition, it is sometimes the case that more than one analyte is concurrently dysregulated, either due to the same physiological condition or resulting from a comorbid (existing simultaneously) related or unrelated physiological condition.

Analyte monitoring in an individual may take place periodically or continuously over a period of time. Periodic analyte monitoring may take place by withdrawing a sample of bodily fluid, such as blood, at one or more time intervals and analyzing ex vivo. Continuous analyte monitoring may be conducted using one or more sensors that remain at least partially implanted within a tissue of an individual, such as dermally, subcutaneously, or intravenously so that analyses may be conducted in vivo. Implanted sensors may collect analyte data at any dictated rate, depending on an individual's particular health needs and/or previously measured analyte levels, for example.

In vivo analyte sensors are typically configured to analyze for a single analyte in order to provide specific analyses, often employing an enzyme to provide the analytical specificity for the given analyte. However, the physiological interplay between various combinations of analytes can make multi-analyte analyses desirable in certain instances, as well. At present, in vivo analysis of multiple analytes may necessitate using a corresponding number of analyte sensors configured for analyzing each analyte. This approach may be inconvenient due to the requirement for an individual to wear multiple analyte sensors. In addition, multiple analyte sensors may represent an unacceptable cost burden for an individual or an insurance provider. There is also an increased opportunity for one of the independent analyte sensors to fail during such sensing protocols.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 2B and 2C show diagrams of illustrative three-electrode analyte sensor configurations having a single working electrode, which are compatible for use in one or more embodiments of the disclosure herein.

FIG. 9A shows two replicates of the response for an electrode containing glucose oxidase and xanthine oxidase layered in separate active areas and spaced apart by a membrane upon exposure to varying ethanol concentrations, in which catalase is present in the active area containing glucose oxidase.

DETAILED DESCRIPTION

Figure 1:
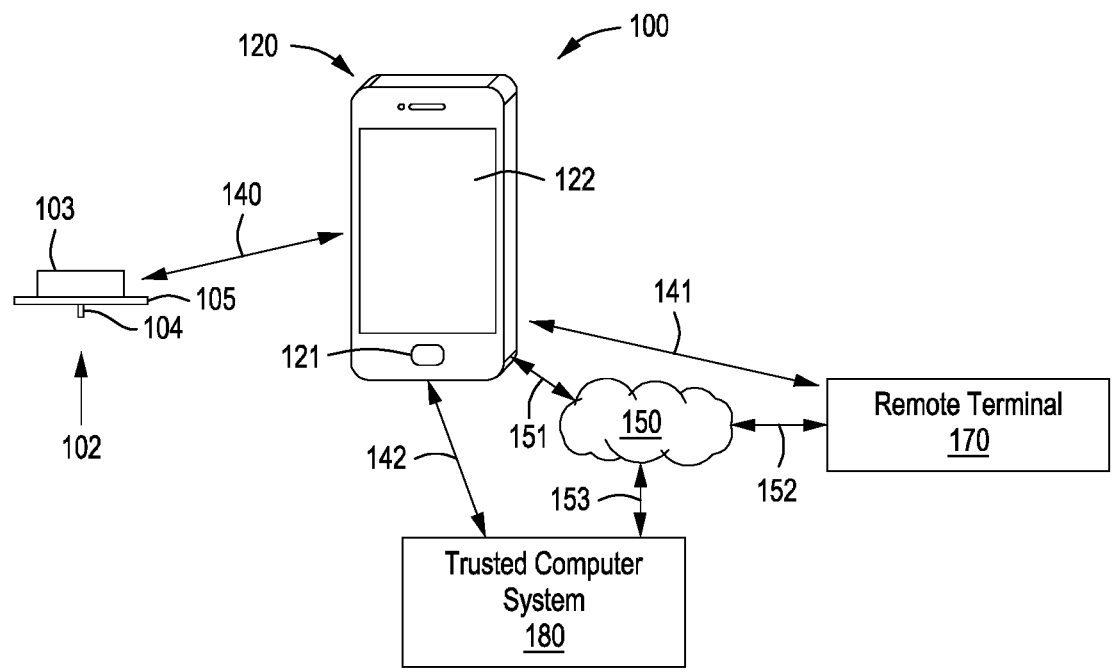
FIG. 1 shows a diagram of an illustrative sensing system that may incorporate an analyte sensor of the present disclosure.

The present disclosure generally describes analyte sensors and methods employing multiple enzymes for detection of at least two different analytes and, more particularly, to analyte sensors and methods employing multiple enzymes for detection of at least glucose and ethanol.

As discussed above, analyte sensors are commonly used to detect a single analyte, typically employing an enzyme having particular specificity for a particular substrate. However, the monitoring of multiple analytes may be complicated by the need to employ a corresponding number of analyte sensors to facilitate the separate detection of each analyte. This approach may be problematic or undesirable, especially when monitoring multiple analytes in vivo, due to issues such as, for example, the cost of multiple analyte sensors, user comfort when wearing multiple analyte sensors, an increased statistical likelihood for failure of one or more individual analyte sensors, and the like.

Glucose-responsive analyte sensors represent a well-studied and still evolving field to aid diabetic individuals in better managing their health. Despite the prevalence of comorbid conditions in diabetic individuals, suitable sensor chemistries for detecting other analytes commonly dysregulated in combination with glucose have lagged behind in development.

The present disclosure provides analyte sensors that are responsive to at least two analytes of interest using a single enzyme-based analyte sensor. More particularly, the present disclosure provides analyte sensors that are responsive to both glucose and ethanol, two analytes that play important roles in diabetes management. As used herein, the term "ethanol" refers to the chemical compound $C_2H_6O$, and is an ingredient in alcoholic beverages; the terms "alcohol" and "ethanol" are used interchangeably herein, unless specified otherwise. Such dual glucose and ethanol sensors are capable of being worn on-body to provide concurrent continuous or near-continuous access to both in vivo glucose and ethanol levels.

Glucose homeostasis, the balance of insulin and glucagon to maintain blood glucose, is critical to the functioning of the central nervous system and various cellular systems that rely on such homeostasis for proper metabolism. Fluctuations in glucose homeostasis (i.e., hyperglycemia, an excess of blood glucose and hypoglycemia, a deficiency of blood glucose) can interfere with organ and cellular operation, at least by specifically interfering with insulin and glucose production, regulation, and action. For example, alcohol may inhibit the production of glucose in the liver, and thus its release therefrom, increasing the risk of moderate or severe hypoglycemia. Alcohol may also reduce the effectiveness of insulin, thereby increasing the risk of moderate or severe hyperglycemia. Thus, the relationship between alcohol and glucose may not directly correlate with each other, is individualistic in many respects (e.g., genetic predispositions), and dependent at least upon exposure time and concentration. Moreover, alcohol may impair an individual's ability to recognize or appreciate symptoms associated with hyperglycemia and hypoglycemia, thereby exacerbating the health risk to the individual.

Knowledge of alcohol-induced alterations in the glycemic control of a diabetic individual, whose glucose levels are naturally dysregulated or otherwise lack homeostasis without intervention, can be of extreme benefit. Although monitoring ethanol levels alone according to the present disclosure may be advantageous, the present disclosure further allows simultaneous, or dual, monitoring of both ethanol and glucose levels, glucose levels of which are typically monitored by diabetic individuals. In doing so, an individual can monitor and correlate their specific ethanol and glucose levels to customize treatment decisions, lifestyle decisions, and the like. Therefore, the present disclosure provides analyte sensors that are responsive to both glucose and ethanol, which may lead to improved health outcomes, particularly for diabetic individuals. In some embodiments, the dual glucose and ethanol responsive sensors of the present disclosure may additionally detect one or more other analytes (e.g., lactate, oxygen, pH, A1c, ketones, drug levels, and the like), without departing from the scope of the present disclosure.

Embodiments of the present disclosure include single analyte sensors comprising at least an ethanol-responsive active area, optionally in combination with a glucose-responsive active area. Although this disclosure discusses dual glucose and ethanol analyte sensors, it is to be appreciated that an analyte sensor comprising only one or more ethanol-responsive active areas (and not in combination with any glucose-responsive active areas) is also within the scope of the present disclosure.

Embodiments disclosed herein comprise glucose- and ethanol-responsive active areas that are present within the tail of a single analyte sensor, thereby allowing both analytes to be monitored concurrently in vivo. As used herein, the term "tail," with reference to a sensor, means a portion of the sensor that comprises analyte-responsive active area(s) and is implanted or otherwise in contact within a tissue of an individual, such as dermally, subcutaneously, or intravenously. The tail may be of any shape or size and may be associated with other tissue-implanted components (e.g., fully implantable analyte sensors), without departing from the scope of the present disclosure. Various physical dispositions of the glucose-responsive active area and the ethanol-responsive active area are possible within the analyte sensors discussed hereinafter, as well as the particular challenges associated with a dual glucose and ethanol sensor. Particular implementations of the present disclosure include sensor architectures in which the glucose-responsive active area and the ethanol-responsive active area may be interrogated separately and concurrently to determine the concentration of each analyte.

The embodiments herein utilize an enzyme system including detection chemistries comprising at least two enzymes that are capable of acting in concert to facilitate detection of at least glucose and ethanol. As used herein, the term "in concert," and grammatical variants thereof, refers to an enzyme reaction system, in which the product of at least a first enzymatic reaction becomes the substrate for at least a second enzymatic reaction, where the final enzymatic reaction serves as the basis for measuring the concentration of a substrate (analyte). Although defined in terms of two coupled enzymatic reactions, it is to be appreciated that more than two enzymatic reactions may be coupled as well in some instances. For example, in some embodiments, the product of a first enzymatic reaction may become the substrate of a second enzymatic reaction, the product of the second enzymatic reaction may become the substrate for a third enzymatic reaction, with the third enzymatic reaction serving as the basis for measuring the concentration of the substrate (analyte) reacted during the first or second enzymatic reaction.

It may be desirable to utilize two or more enzymes acting in concert with one another to detect a given analyte of interest when a single enzyme is unable to facilitate detection. Situations in which a single enzyme may be ineffective for promoting analyte detection include, for example, those in which an enzyme is inhibited by one or more products of the enzymatic reaction, is unable to cycle between an oxidized state and reduced state when disposed within an analyte sensor, and/or is unknown for promoting a reaction pathway needed to facilitate detection.

Combining a glucose-responsive active area and an ethanol-responsive active area into a single analyte sensor may pose several hurdles. In particular, glucose-responsive analyte sensors commonly employ oxidation-reduction mediators, which may not freely exchange electrons with enzymes necessary for detection of ethanol. Glucose-responsive analyte sensors may additionally employ a single mass transport limiting polymer membrane to aid in avoiding sensor overload (saturation) and facilitate accurate glucose measurement. The mass transport-limiting layer which is appropriate for glucose may not be appropriate for alcohol, due to their considerably different diffusivities and concentrations. Additional hurdles include differences in analyte sensitivity and potential incompatibility of one or more of the enzymes to a given set of analysis conditions.

The present disclosure further provides membrane compositions, deposition configurations, and deposition methods to facilitate concurrent detection of glucose and ethanol. Specifically, in some embodiments, the present disclosure provides certain dual-layer membrane configurations that facilitate enhanced ethanol detection without hindering glucose detection. As used herein, the term "dual-layer membrane" refers to a membrane having two deposition layers that overcoat at least a working electrode and an active area, which may be the same or different in composition. That is, a dual-layer membrane may be homogeneous (of the same chemistry) in composition or heterogeneous (of different chemistries) in composition and is describe with reference to analyte sensor components in which it overcoats. As used herein, a "single-layer membrane" refers to a membrane having one deposition layer that overcoats at least a working electrode and an active area and is homogeneous composition. In some embodiments, the configurations of the dual glucose and ethanol sensors described herein permit a homogeneous single-layer membrane to be disposed (overcoat) over both, at least one glucose-responsive active area and at least one ethanol-responsive active area. In other embodiments, the configurations of the dual glucose and ethanol sensors described herein permit a homogeneous single-layer membrane to be disposed over at least one glucose-responsive active area and a homogeneous or heterogeneous dual-layer membrane to be disposed over at least one ethanol-responsive active area.

Before describing the specific analyte sensors of the present disclosure in more detail, a brief overview of suitable in vivo analyte sensor configurations and sensor systems is provided so that the embodiments of the present disclosure may be better understood. It is to be understood that any of the sensor systems and analyte sensor configurations described hereinafter may feature multiple enzymes, in accordance with the various embodiments of the present disclosure, and are not limited to the specific configurations described herein.

FIG. 1 shows a diagram of an illustrative sensing system that may incorporate an analyte sensor of the present disclosure such as an analyte sensor comprising a glucose-responsive active area and an ethanol-responsive active area. As shown, sensing system 100 includes sensor control device 102 and reader device 120 configured to communicate with one another over a local communication path or link 140, which may be wired or wireless, uni- or bi-directional, and encrypted or non-encrypted. Reader device 120 may constitute an output medium for viewing various information, such as analyte concentrations, analyte trends, alerts, and/or notifications determined by sensor 104 or a processor associated therewith, as well as allowing for one or more user inputs, according to some embodiments. Reader device 120 may be a multi-purpose smartphone or a dedicated electronic reader instrument, for example. While only one reader device 120 is shown, multiple reader devices 120 may be present in certain instances and in communication with sensor control device 102 (e.g., to allow multiple users access to analyte levels). Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer systems 180 with or without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225, incorporated herein by reference in its entirety.

Any suitable electronic communication protocol may be used for each of the communication paths or links, such as near field communication (NFC), radio frequency identification (RFID), BLUETOOTH® or BLUETOOTH® Low Energy protocols, WiFi, or the like. Reader device 120, and/or remote terminal 170, and/or trusted computer system 180, and/or an additional one or more reader devices, as described above, may be accessible, according to some embodiments, by individuals other than a primary user who have an interest in the user's analyte levels. Reader device 120 may comprise display 122 and optional input component 121. Display 122 may comprise a touch-screen interface, according to some embodiments for outputting information related to the sensor control device 102 and user input, for example.

Sensor control device 102 includes sensor housing 103, which may house circuitry and a power source for operating sensor 104. Optionally, the power source and/or active circuitry may be omitted, and the sensor control device 102 may be otherwise self-powered. A processor (not shown) may be communicatively coupled to sensor 104, with the processor being physically located within sensor housing 103 and/or reader device 120. Sensor 104 protrudes from the underside of sensor housing 103 and extends through an adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode and one or more active areas (sensing regions/spots or sensing layers, which may be of any shape or size) located upon the at least one working electrode and that are active for sensing one or more analytes of interest, such as glucose and/or ethanol. In some embodiments, the active areas are in the form of one or more discrete spots (e.g., one to about 10 sports, or more), which may range in size from about 0.01 mm² to about 1 mm², encompassing any value and subset therebetween although larger or smaller individual active area spots are also contemplated herein.

One or more of the active areas may comprise multiple enzymes overcoated with one or more membranes, according to some embodiments of the present disclosure. The active areas may include a polymeric material to which at least some of the enzymes are chemically bonded (e.g., covalently bonded, ionically bonded, and the like) or otherwise immobilized (e.g., unbound in a matrix), according to some embodiments. In some embodiments, each active area may further comprise an electron transfer agent to facilitate detection of the analyte of interest.

In various embodiments of the present disclosure, the analyte(s) of interest (e.g., glucose and ethanol) may be monitored in any biological fluid of interest such as dermal fluid, interstitial fluid, plasma, blood, lymph, synovial fluid, cerebrospinal fluid, saliva, bronchoalveolar lavage, amniotic fluid, and the like. In particular embodiments, analyte sensors of the present disclosure may be adapted for assaying dermal fluid or interstitial fluid to determine concentrations of glucose and/or ethanol in vivo.

With continued reference to FIG. 1, sensor 104 may automatically forward data to reader device 120. For example, analyte concentration data (e.g., glucose and/or ethanol concentrations) may be communicated automatically and periodically, such as at a certain frequency as data is obtained or after a certain time period has passed, with the data being stored in a memory until transmittal (e.g., every several seconds, every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a patient does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104. While automatic and non-automatic data transfer from sensor 104 has been described with reference to reader device 120, such transfer mechanisms are equally applicable to remote terminal 170 and/or trusted computer system 180, without departing from the scope of the present disclosure.

An introducer may be present transiently to promote introduction of sensor 104 into a tissue. In illustrative embodiments, the introducer may comprise a needle or similar sharp object. It is to be recognized that other types of introducers, such as sheaths or blades, may be present in alternative embodiments. More specifically, the needle or other introducer may transiently reside in proximity to or concurrently with (e.g., externally surrounding) sensor 104 prior to tissue insertion and then be withdrawn afterward. While present, the needle or other introducer may facilitate insertion of sensor 104 into a tissue by opening an access pathway for sensor 104 to follow. For example, the needle or other introducer may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable introducers include needles that may be solid or hollow, beveled or non-beveled, circular or non-circular in cross-section, and the like. In more particular embodiments, suitable needles may be comparable in cross-sectional diameter and/or tip design to an acupuncture needle, which may have a cross-sectional diameter of about 150 to about 300 micrometers (e.g., 250 micrometers). It is to be recognized, however, that suitable needles may have a larger or smaller cross-sectional diameter if needed for particular applications.

In some embodiments, a tip of an introducer (while present) may be angled over the terminus of sensor 104, such that the introducer penetrates a tissue first and opens an access pathway for sensor 104. In other illustrative embodiments, sensor 104 may reside within a lumen or groove of the introducer, with the introducer similarly opening an access pathway for sensor 104. In either case, the introducer is subsequently withdrawn after facilitating sensor insertion.

The analyte sensors disclosed herein may feature active areas of different types (i.e., a glucose-responsive active area and an ethanol-responsive active area) upon a single working electrode (e.g., on a same or opposite side of a single working electrode) or upon two or more separate working electrodes. Single working electrode sensor configurations may employ two-electrode or three-electrode detection motifs, according to various embodiments of the present disclosure and as described further herein. Sensor configurations featuring a single working electrode are described hereinafter in reference to FIGS. 2A-2C. Each of these sensor configurations may suitably incorporate a glucose-responsive active area and an ethanol-responsive active area according to various embodiments of the present disclosure. Sensor configurations featuring multiple working electrodes are described thereafter in reference to FIGS. 3 and 4A-4D. When multiple working electrodes are present, one or more glucose-responsive active areas may be disposed upon a first working electrode and one or more ethanol-responsive active areas may be disposed upon a second working electrode. Sensor configurations employing multiple working electrodes may be particularly advantageous for incorporating both a glucose-responsive active area and an ethanol-responsive active area according to the disclosure herein, since mass transport-limiting membranes having differing compositions and/or different permeability values may be deposited more readily during manufacturing when the active areas are separated and/or spaced apart in this manner. Particular sensor configurations featuring multiple working electrodes disposed in a manner to facilitate deposition of mass transport-limiting membranes having differing compositions, particularly by dip coating, upon each working electrode are shown in FIGS. 4A-4C. Suitable techniques for depositing the mass transport-limiting membranes disclosed herein include, for example, by spray coating, painting, inkjet printing, stenciling, roller coating, dip coating, or the like, and any combination thereof.

When a single working electrode is present in an analyte sensor, three-electrode sensor configurations may comprise a working electrode, a counter electrode, and a reference electrode. Related two-electrode sensor configurations may comprise a working electrode and a second electrode, which may function as both a counter electrode and a reference electrode (i.e., a counter/reference electrode). In both two-electrode and three-electrode configurations, both the glucose-responsive active area and the ethanol-responsive active area may be in contact with (e.g., disposed upon) the single working electrode. In some embodiments, the various electrodes may be at least partially stacked (layered) upon one another and/or laterally spaced apart from one another upon the sensor tail. Suitable sensor configurations may be substantially flat in shape or substantially cylindrical in shape, with the glucose-responsive active area and the ethanol-responsive active area being spaced apart upon the working electrode. In all of the sensor configurations disclosed herein, the various electrodes may be electrically isolated from one another by one or more dielectric materials or similar insulators.

Analyte sensors featuring multiple working electrodes may additionally be suitable for use in the embodiments described herein. Such analyte sensors comprise at least two working electrodes and at least one additional electrode, which may function as a counter/reference electrode for each of the working electrodes. In other embodiments, a first additional electrode may function as a counter electrode for each of the multiple working electrodes and a second additional electrode may function as a reference electrode for each of the multiple working electrodes.

The various analyte sensors described herein may be operable for assaying an analyte (e.g., at least glucose and ethanol) by any of coulometric, amperometric, voltammetric, or potentiometric electrochemical detection techniques.

Figure 2A:
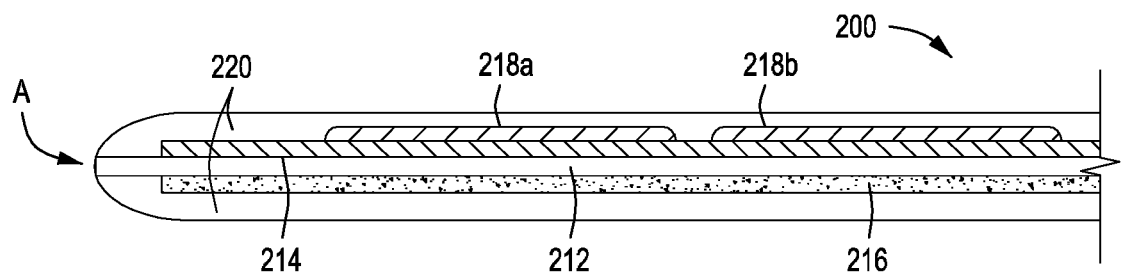
FIG. 2A shows a diagram of an illustrative two-electrode analyte sensor configuration having a single working electrode, which is compatible for use in one or more embodiments of the disclosure herein.

FIG. 2A shows a cross-sectional diagram of an illustrative two-electrode analyte sensor configuration having a single working electrode. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active areas 218a and 218b (i.e., a glucose-responsive active area and an ethanol-responsive active area) are laterally spaced apart from one another upon the surface of working electrode 214. In the various sensor configurations shown herein, active areas 218a and 218b may comprise multiple spots or a single spot configured for the detection of each analyte. Moreover, in some embodiments, active areas 218a and 218b may be disposed on opposite sides of the single electrode (not shown), without departing from the scope of the present disclosure.

Referring still to FIG. 2A, membrane 220 overcoats at least active areas 218a and 218b and may optionally overcoat some or all of working electrode 214 and/or counter/reference electrode 216, the entirety of analyte sensor 200, or at least the entirety of the tail portion of analyte sensor 200 comprising active areas 218a and 218b. One or both faces of analyte sensor 200 may be overcoated with membrane 220. Membrane 220 may comprise one or more polymeric membrane materials (membrane polymers) having suitable capabilities for limiting analyte flux to active areas 218a and 218b. Although not readily apparent in FIG. 2A, the composition of membrane 220 may vary at active areas 218a and 218b in order to differentially regulate the analyte flux at each location, as described further herein and/or to separate one or more components of a concerted enzymatic reaction system (e.g., if certain reactants or products of the system are inhibitory to analyte detection). For example, membrane 220 may be sprayed and/or printed onto active areas 218a and 218b, such that the composition and/or layering of membrane 220 differs at each location.

In some embodiments, membrane 220 may be deposited by dip coating starting from end A of analyte sensor 200. Specifically, end A of analyte sensor 200 may be dipped in a first coating formulation to overcoat active area 218a. After partially curing the first coating formulation upon active area 218a, end A of analyte sensor 200 may be dipped in a second coating formulation to overcoat both active areas 218a and 218b with the second coating formulation. As such, membrane 220 may be a dual-layer at active area 218a and homogeneous at active area 218b. In other embodiments, end A of analyte sensor 200 may be dipped in a first coating formulation to overcoat both active areas 218a and 218b, and after partially curing, end A may be dipped in a second coating formulation to overcoat only one of active area 218a or 218b. The first and second coating formulation may be identical or different in composition, without departing from the scope of the present disclosure.

FIGS. 2B and 2C show cross-sectional diagrams of illustrative three-electrode sensor configurations having a single working electrode, which are compatible for use in some embodiments of the disclosure herein. Three-electrode sensor configurations featuring a single working electrode may additionally be similar to that shown for analyte sensor 200 in FIG. 2A, except for the inclusion of additional electrode 217 in analyte sensors 201 and 202 (FIGS. 2B and 2C). With additional electrode 217, electrode 216 may function as either a counter electrode or a reference electrode, and additional electrode 217 may fulfill the other electrode function not otherwise accounted for. Working electrode 214 continues to fulfill its original function in either case. Additional electrode 217 may be disposed upon either working electrode 214 or electrode 216, with a separating layer of dielectric material in between each. For example, as depicted in FIG. 2B, electrodes 214, 216 and 217 are located upon the same face of substrate 212 and are electrically isolated from one another by dielectric layers 219a, 219b, and 219c. Alternately, at least one of electrodes 214, 216, and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with analyte sensor 200 shown in FIG. 2A, active areas 218a and 218b in analyte sensors 201 and 202 are disposed laterally spaced apart from one another upon working electrode 214 in the sensor configurations of FIGS. 2B and 2C, but may otherwise be spaced apart in any other configuration (e.g., on opposite sides of the working electrode).

Like analyte sensor 200 (FIG. 2A), membrane 220 may also overcoat active areas 218a and 218b, as well as other sensor components, in analyte sensors 201 and 202. Additional electrode 217 may be overcoated with membrane 220 in some embodiments. Although FIGS. 2B and 2C have depicted all of electrodes 214, 216, and 217 as being overcoated with membrane 220, it is to be recognized that only working electrode 214 or only a portion of working electrode 214 comprising active areas 218a and 218b may be overcoated in some embodiments. Moreover, the thickness of membrane 220 at each of electrodes 214, 216, and 217 may be the same or different, and may be layered upon each of electrodes 214, 216, and 217 identically or differently, as previously described. As in two-electrode sensor configurations (FIG. 2A), one or both faces of analyte sensors 201 and 202 may be overcoated with membrane 220 in the sensor configurations of FIGS. 2B and 2C, the entirety of analyte sensors 201 and 202 may be overcoated, or only active areas 218a and 218b may be overcoated. Moreover, the membrane 220 may vary compositionally at active areas

218*a* and 218*b* to control flux to the active areas and/or to isolate various components of a concerted enzymatic reaction system, such as by dip coating the membrane 220 from end A to deposit a dual-layer over one of active areas 218*a* and 218*b* and a homogeneous layer over the other active area, for example. Accordingly, the three-electrode sensor configurations shown in FIGS. 2B and 2C should be understood as being non-limiting of the embodiments disclosed herein, with alternative electrode and/or layer configurations remaining within the scope of the present disclosure.

FIGS. 3, 4 6A, 6B, and 8 depict sensor configurations having multiple working electrodes. Although the following description is primarily directed to analyte sensor configurations having two working electrodes, it is to be appreciated that more than two working electrodes may be successfully incorporated through an extension of the disclosure herein. Additional working electrodes may allow additional active area(s) and corresponding sensing capabilities to be imparted to analyte sensors having such features, such as to impart additional sensing capabilities other than glucose and ethanol sensing.

Figure 3:
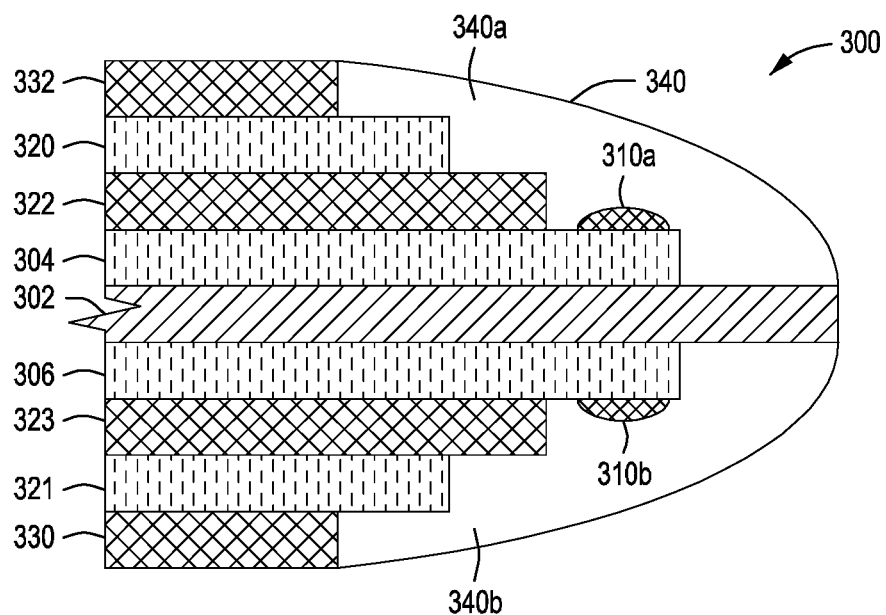
FIG. 3 shows a diagram of an illustrative analyte sensor configuration having two working electrodes, a reference electrode, and a counter electrode, which is compatible for use in one or more embodiments of the disclosure herein.

FIG. 3 shows a cross-sectional diagram of an illustrative sensor configuration having two working electrodes, a reference electrode, and a counter electrode, which is compatible for use in one or more embodiments of the disclosure herein. As shown in FIG. 3, analyte sensor 300 includes working electrodes 304 and 306 disposed upon opposite faces of substrate 302. Active area 310*a* is disposed upon the surface of working electrode 304, and active area 310*b* is disposed upon the surface of working electrode 306. Each of active areas 310*a* and 310*b* may be either a glucose-responsive active area or an ethanol-responsive active area, thereby permitting dual detection of such analytes, according to various embodiments of the present disclosure. Counter electrode 320 is electrically isolated from working electrode 304 by dielectric layer 322, and reference electrode 321 is electrically isolated from working electrode 306 by dielectric layer 323. Outer dielectric layers 330 and 332 are positioned upon reference electrode 321 and counter electrode 320, respectively. Membrane 340 may overcoat at least active areas 310*a* and 310*b*, according to various embodiments, with other components of analyte sensor 300 or the entirety of analyte sensor 300 optionally being overcoated with membrane 340, as well. Again, membrane 340 may vary compositionally or be disposed in one or more layers at active areas 310*a* and 310*b*, as previously described. For example, different membrane formulations or layers of one or more formulations may be sprayed and/or printed onto the opposing faces of analyte sensor 300. Dip coating techniques may also be appropriate, particularly for depositing a dual-layer membrane upon at least one of active areas 310*a* and 310*b*.

For example, the active area 310*a* or 310*b* may be a glucose-responsive active area, and the other an ethanol-responsive active area. As an example, where active area 310*a* is a glucose-responsive active area, membrane 340*a* may overcoat 310*a* and be a transport limiting membrane compatible with glucose sensing. In such example, active area 310*b* is an ethanol-responsive active area, and membrane 340*b* may overcoat 310*a* and be a transport limiting membrane compatible with ethanol sensing (see FIG. 5A). That is, membrane 340 may be comprised of two separate membrane compositions 340*a*, 340*b* coating active areas 340*a*, 310*b* that are configured for glucose and ethanol sensing, respectively. In some embodiments, the membrane compositions 340*a*, 340*b* may be of the same or different compositions, provided that they are compatible with the analyte to be detected by their respective analyte responsive active areas. It is believed that when membrane 340*a*, 340*b* are of the same composition, they are likely to have different thicknesses to enable the desired analyte detection. In preferred embodiments, the membranes 340*a*, 340*b* may be of different compositions to better facilitate tailored detection, separately, of glucose and ethanol, respectively.

Alternative sensor configurations having multiple working electrodes and differing from that shown in FIG. 3 may feature a counter/reference electrode instead of separate counter and reference electrodes 320 and 321, and/or feature layer and/or membrane arrangements varying from those expressly depicted. For example, the positioning of counter electrode 320 and reference electrode 321 may be reversed from that depicted in FIG. 3. In addition, working electrodes 304 and 306 need not necessarily reside upon opposing faces of substrate 302 in the manner shown in FIG. 3.

Figure 4:
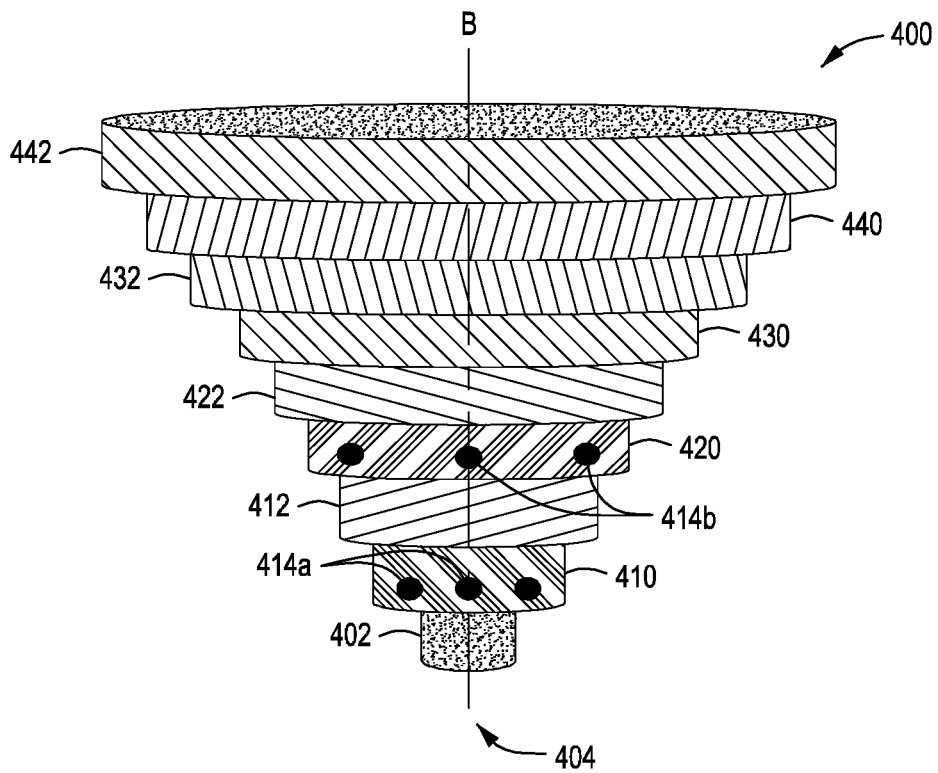
FIG. 4 shows a perspective view of an illustrative sensor configuration in which multiple electrodes are substantially cylindrical and are disposed concentrically with respect to one another about a central substrate, according to one or more embodiments of the present disclosure.

Although suitable sensor configurations may feature electrodes that are substantially planar in character, it is to be appreciated that sensor configurations featuring non-planar electrodes may be advantageous and particularly suitable for use in the disclosure herein. In particular, substantially cylindrical electrodes that are disposed concentrically with one another may facilitate deposition of a mass transport-limiting membrane, as described herein. FIG. 4 shows perspective views of analyte sensors featuring substantially cylindrical electrodes that are disposed concentrically with respect to one another. Although FIGS. 4 depicts sensor configurations featuring two working electrodes, it is to be appreciated that similar sensor configurations having either one working electrode or more than two working electrodes are possible through extension of the disclosure herein.

FIG. 4 shows a perspective view of an illustrative sensor configuration in which multiple electrodes are substantially cylindrical and are disposed concentrically with respect to one another about a central substrate. As shown, analyte sensor 401 includes central substrate 402 about which all electrodes and dielectric layers are disposed concentrically with respect to one another. In particular, working electrode 410 is disposed upon the surface of central substrate 402, and dielectric layer 412 is disposed upon a portion of working electrode 410 distal to sensor tip 404. Working electrode 420 is disposed upon dielectric layer 412, and dielectric layer 422 is disposed upon a portion of working electrode 420 distal to sensor tip 404. Counter electrode 430 is disposed upon dielectric layer 422, and dielectric layer 432 is disposed upon a portion of counter electrode 430 distal to sensor tip 404. Reference electrode 440 is disposed upon dielectric layer 432, and dielectric layer 442 is disposed upon a portion of reference electrode 440 distal to sensor tip 404. As such, exposed surfaces of working electrode 410, working electrode 420, counter electrode 430, and reference electrode 440 are spaced apart from one another along longitudinal axis B of analyte sensor 400. It is to be appreciated that the order of working electrode 410, working electrode 420, counter electrode 430, and reference electrode 440 is non-limiting. Moreover, counter electrode 430 and reference electrode 440 may be combined into a single electrode in some embodiments.

Referring still to FIG. 4, active areas 414*a* and 414*b* are disposed upon the exposed surfaces of working electrodes 410 and 420, respectively, thereby allowing contact with a fluid to take place for sensing of glucose and/or ethanol to take place, optionally in further combination with other analytes. Although active areas 414*a* and 414*b* have been depicted as three discrete, circular spots in FIG. 4 (as well as FIGS. 6A and 6B), it is to be appreciated that fewer or greater than three spots may be present in alternative sensor configurations, and the shape of the spots may be non-circular (e.g., oval, square, polygonal, and the like) in alternative sensor configurations.

FIGS. 3, 6A, 6B, and 7 show various membrane configurations of an analyte sensor for concurrently detecting glucose and ethanol, according to one or more embodiments of the present disclosure. Such embodiments may utilize a dual-layer membrane, for example, to facilitate separation of various sensing components forming part of a concerted enzymatic reaction system that would otherwise inhibit analyte sensing if in coexistence. For example, as stated above, the product of ethanol oxidation is strongly inhibitory to an enzyme required for its detection such that a single-layer membrane may be ineffective to permit ethanol detection. Separation of such components using a dual-layer membrane is necessary to permit accurate ethanol sensing when such a concerted enzymatic reaction system is selected for use in ethanol sensing. Prior to discussion of various membrane configurations suitable for use with the analyte sensor embodiments described herein, concerted enzymatic reaction systems for use in a dual glucose and ethanol sensor will be first discussed.

In some embodiments, an analyte sensor containing concerted enzymatic reaction systems for the detection of ethanol may utilize a first enzyme of alcohol oxidase (AOX) and a second enzyme of xanthine oxidase (XOX). Cooperativity between alcohol oxidase and xanthine oxidase for detecting ethanol (and other non-ethanol alcohols with both enzymes disposed upon a working electrode is explained in further detail hereinafter. In certain embodiments of the present disclosure, the xanthine oxidase is covalently bonded to a polymer in the active area, and the alcohol oxidase is not covalently bonded to the polymer. In other embodiments, both xanthine oxidase and an electron transfer agent may be covalently bonded to the polymer, and the alcohol oxidase is not covalently bonded to the polymer. Catalase may be present as a stabilizer with this pair of enzymes.

Alcohol oxidase interacts with ethanol to form acetaldehyde and hydrogen peroxide. Other alcohols react to form aldehydes with a corresponding higher or lower carbon count. Advantageously, alcohol oxidase only catalyzes the forward conversion of ethanol into acetaldehyde (as opposed to performing the reaction reversibly, such as is the case for alcohol dehydrogenase), which may be favorable for use of this enzyme in an analyte sensor. Moreover, alcohol oxidase contains a strongly bound flavin co-factor, such that exogenous co-factors need not necessarily be combined with alcohol oxidase to render the enzyme active for promoting alcohol oxidation.

In principle, alcohol oxidase alone could be employed for ethanol detection in an analyte sensor by assaying either the acetaldehyde or hydrogen peroxide products produced in the enzymatic reaction. There are two potential issues with this approach, however. First, both acetaldehyde and hydrogen peroxide are inhibitory toward alcohol oxidase. Thus, if these compounds are not cleared from the sensor environment, the alcohol oxidase becomes inactive for promoting ethanol oxidation, thereby leaving the analyte sensor non-functional or sub-optimal for assaying ethanol. Moreover, if acetaldehyde and hydrogen peroxide become sequestered or undergo quenching with other agents, there is no longer a species available for electrochemical detection. Second, alcohol oxidase does not freely exchange electrons with oxidation-reduction mediators, other than molecular oxygen. As such, electron transfer agents associated with a polymer in the active area of an analyte sensor, such as osmium and other transition metal complexes discussed herein, may be ineffective for cycling alcohol oxidase from an inactive reduced state into an oxidized state that is reactive with ethanol. Thus, although alcohol oxidase may be optionally covalently bonded to the polymer, there are no particular benefits to the electron transfer process in doing so. That is, covalent bonding of alcohol oxidase to the polymer does not aid in promoting electron transfer with the electron transfer agent.

A concerted enzyme system comprising alcohol oxidase and xanthine oxidase disposed directly upon a working electrode, particularly together in a given active area, may overcome at least some of the foregoing challenges associated with ethanol detection using an analyte sensor employing alcohol oxidase. Acetaldehyde and other aldehydes may serve as a substrate for xanthine oxidase, with the acetaldehyde being enzymatically converted to acetic acid. Thus, xanthine oxidase may clear acetaldehyde from the sensor environment, thereby precluding acetaldehyde-based inactivation of the alcohol oxidase. Catalase may be present in the active area to clear hydrogen peroxide (e.g., as a catalase-hydrogen peroxide complex), thereby precluding inactivation of the alcohol oxidase with this species. In addition, unlike alcohol oxidase, xanthine oxidase may exchange electrons with osmium and other transition metal complexes associated with a polymer in the active area of the analyte sensor. As such, xanthine oxidase may cycle between its oxidized and reduced forms, thereby allowing the analyte sensor to maintain an active sensing state. Detection of ethanol in the foregoing analyte sensors is therefore based upon the enzymatic reaction of xanthine oxidase with acetaldehyde, the enzymatic reaction product of ethanol rather than ethanol itself. Moreover, by configuring the enzymes in the analyte sensor in the foregoing manner, the alcohol oxidase may undergo re-oxidation with molecular oxygen to maintain its activity.

Figure 5A:
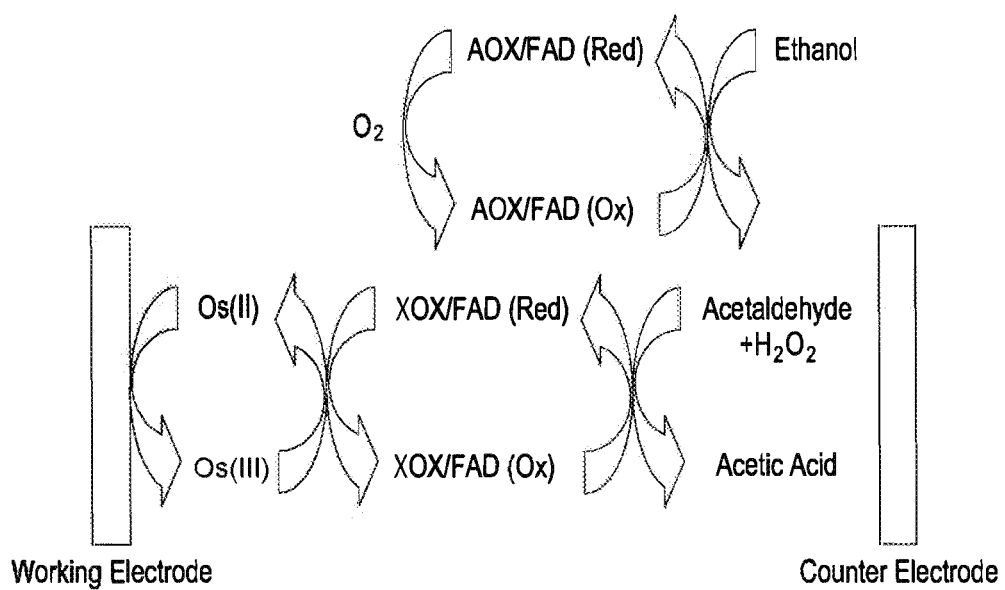
FIG. 5A shows a concerted enzymatic reaction system associated with ethanol detection using alcohol oxidase and xanthine oxidase located directly upon a working electrode, according to one or more embodiments of the present disclosure.

FIG. 5A shows the concerted enzymatic reaction system associated with ethanol detection using alcohol oxidase and xanthine oxidase disposed directly upon a working electrode, according to various embodiments of the present disclosure. Xanthine oxidase is covalently bonded to a polymer in the active area of the analyte sensor, and alcohol oxidase is non-covalently associated with the polymer in the active area. In addition to xanthine oxidase, an osmium complex or other transition metal complex capable of exchanging electrons with this enzyme is also covalently bonded to the polymer. As shown in FIG. 5A, ethanol reacts with oxidized (active) alcohol oxidase in the presence of a flavin co-factor (FAD-already bonded with the alcohol oxidase), thereby forming reduced alcohol oxidase, acetaldehyde, and hydrogen peroxide. The reduced alcohol oxidase may be re-oxidized with molecular oxygen as shown to return the alcohol oxidase to its catalytically active oxidized form.

Referring still to FIG. 5A, the acetaldehyde enzymatically formed from ethanol then undergoes a subsequent reaction with the oxidized form of xanthine oxidase in the presence of the flavin co-factor that is present natively with the enzyme. Acetic acid is formed in this process and the xanthine oxidase is transformed into a reduced state. The reduced xanthine oxidase may then react with the transition metal electron transfer agent associated with the polymer to transfer electrons to the working electrode, thereby producing a current and regenerating the oxidized form of xanthine oxidase. Although not shown in FIG. 5A, hydrogen peroxide may be separately cleared from the sensor environment by catalase that is present in the active area.

As can be appreciated from FIG. 5A, the amount of enzymatically formed acetaldehyde is proportional to the amount of ethanol originally present. As such, the current produced at the working electrode during the xanthine oxidase oxidation of the acetaldehyde may be proportional to the amount of acetaldehyde present, and, by extension, the amount of ethanol. Correlation of the working electrode current to the ethanol concentration may take place by referring to a lookup table of currents at known ethanol concentrations or by utilizing a calibration curve.

Accordingly, in some embodiments, the present disclosure provides ethanol-responsive active areas (e.g., for use in the dual glucose and ethanol analyte sensors described herein) based upon a concerted enzymatic reaction of alcohol oxidase and xanthine oxidase. More specifically, the present disclosure provides analyte sensors comprising a sensor tail including at least a working electrode, and at least one ethanol-responsive active area disposed upon a surface of the working electrode, wherein the at least one active area comprises alcohol oxidase, xanthine oxidase, catalase, a polymer, and an electron transfer agent. The electron transfer agent and the xanthine oxidase may be covalently bonded to the polymer, and the alcohol oxidase is not covalently bonded to the polymer, according to particular embodiments. The alcohol oxidase and the xanthine oxidase are capable of acting in concert to generate a signal at the working electrode that is proportional to an alcohol concentration. More specifically, the alcohol oxidase and the xanthine oxidase are both disposed directly upon the working electrode in order to accomplish the foregoing.

Although multiple enzymes of a concerted enzymatic reaction system located in a single active area of an analyte sensor may interact in concert with one another to determine an analyte concentration, separation of components (e.g., reactants and/or products) of such concerted enzymatic reaction systems using separate active areas may sometimes facilitate improved and/or more stabilized analyte detection. In some embodiments, analyte sensor configurations may contain multiple enzymes spread over separate active areas, where one of the active areas may be isolated from the working electrode so that electron transfer to the working electrode takes place from only one of the active areas. For example, the active area isolated from the working electrode may promote an enzymatic reaction of an analyte of interest to produce a reaction product (substrate) that is itself reactive with the enzyme in the active area in direct contact with the working electrode; a signal associated with the enzymatic reaction taking place in the active area in direct contact with the working electrode then provides a basis for detecting the analyte. Correlation of the signal to the analyte concentration may be accomplished in any of various manners discussed herein.

Figure 5B:
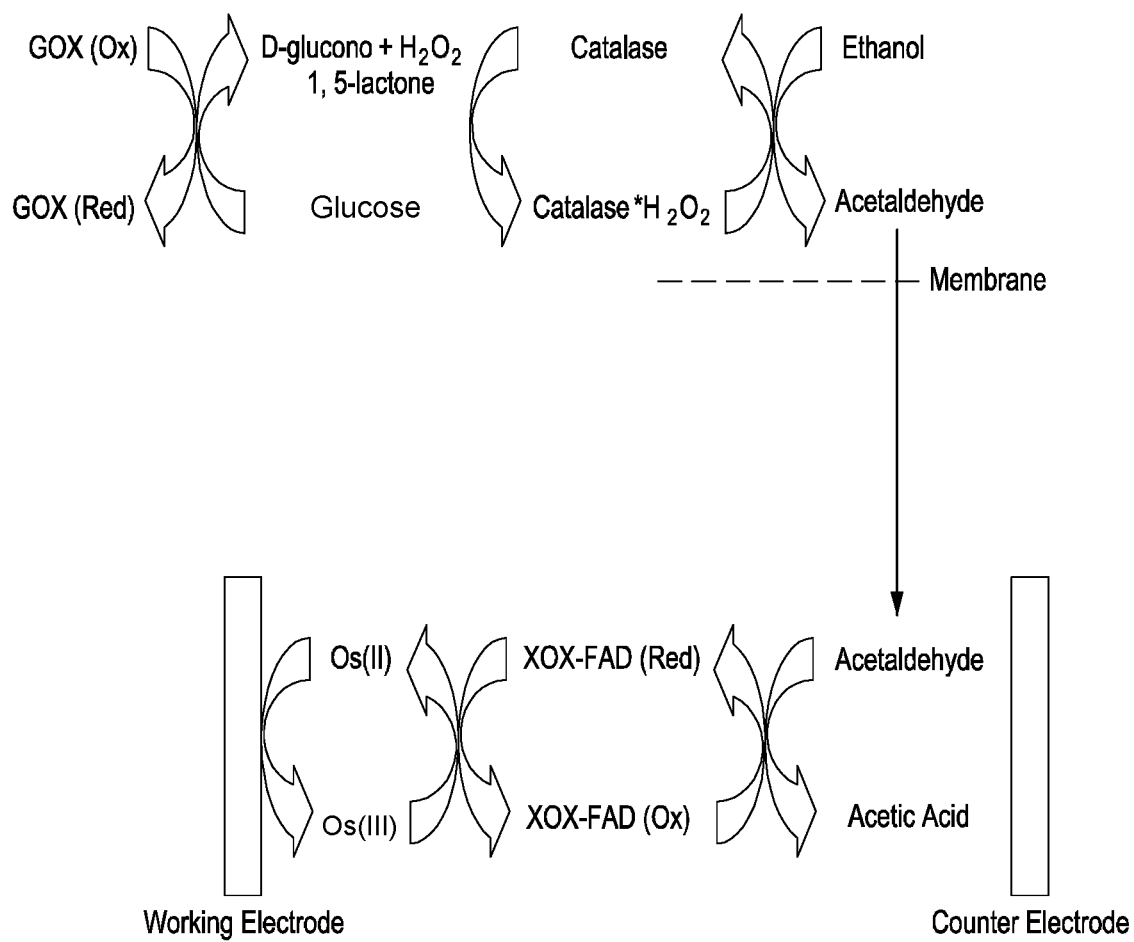
FIG. 5B shows a concerted enzymatic reaction system associated with ethanol detection using glucose oxidase, catalase, and xanthine oxidase, in which glucose oxidase is remote from a working electrode and xanthine oxidase is located directly upon the working electrode, according to one or more embodiments of the present disclosure.

More specifically, FIG. 5B shows a concerted enzymatic reaction system associated with ethanol detection using glucose oxidase (GOX) and xanthine oxidase, as further mediated by catalase, when only the xanthine oxidase or xanthine oxidase and catalase is disposed upon the surface of a working electrode, according to various embodiments of the present disclosure. Catalase may also serve as a stabilizer for this pair of enzymes. That is, the components of the concerted enzymatic reaction system for detecting ethanol may be located in separate active area polymers to overcome certain issues associated with comingling of the components of the concerted enzymatic reaction system. For example, glucose oxidase must be separated from a working electrode to prevent the glucose oxidase from reacting to generate current, such as by reaction with an electron transfer agent (e.g., osmium or other transition metal) located in an active area in direct contact with a working electrode. If the glucose oxidase is not separated from the working electrode, inaccurate or otherwise aberrant ethanol measurements may result, since glucose oxidation provides a signal contribution. Accordingly, to facilitate detection of ethanol, as well as to overcome the issues associated with ethanol detection using alcohol oxidase and xanthine oxidase, as discussed above, the present disclosure provides an ethanol sensor comprising two active areas and a dual-layer membrane configuration, such that the two active areas are separated.

The concerted enzymatic reaction system shown in FIG. 5B is dependent upon glucose and ethanol being co-present with one another in a fluid during analysis. Because glucose is a ubiquitous biological nutrient, it is frequently found co-present with other analytes, including ethanol, when assaying a biological fluid.

With continued reference to FIG. 5B, glucose oxidase is present in an active area (e.g., active area 702a or 702b of FIG. 7) and converts exogenous glucose into D-gluconolactone-1,5-dione and hydrogen peroxide. Unlike ethanol-responsive active areas featuring detection based upon a concerted enzymatic reaction between alcohol oxidase and xanthine oxide (FIG. 5A), the catalase plays a more active role in the concerted enzymatic reaction system depicted in FIG. 5B. Namely, catalase reacts with the hydrogen peroxide to form a catalase-hydrogen peroxide complex (the same peroxide-clearing function exhibited by catalase in the concerted enzymatic reaction of alcohol oxidase and xanthine oxidase) in an isolated active area, with the complex subsequently reacting with ethanol to form acetaldehyde in the same isolated active area. The acetaldehyde formed in the one active area upon reacting ethanol with catalase-hydrogen peroxide complex permeates through a membrane to a second active area, the membrane separating the active areas (e.g., active areas 702a and 702b of FIG. 7). The membrane may comprise crosslinked polyvinylpyridine, which is permeable to acetaldehyde, for example. The acetaldehyde then reacts with xanthine oxidase in a second active area (e.g., active areas 702a or 702b of FIG. 7) to form acetic acid in a manner similar to that described above for FIG. 5A. An immobilized or chemically bonded electron transfer agent (e.g., an osmium complex or other transition metal complex) may preferably be present within the active area with the xanthine oxidase for exchanging electrons to facilitate the acetic acid formation, which correlates to ethanol levels. Catalase may also be optionally present within the either active area to act as a stabilizer. Further, in addition to the membrane depicted in FIG. 5B, a second membrane may overcoat the two active areas forming a dual-layer membrane structure, where the second membrane is permeable to both glucose and ethanol.

Alternatively, catalase may be present in an active area comprising xanthine oxidase, in which case the hydrogen peroxide formed in the active area comprising glucose oxidase may diffuse through a membrane into the active area comprising xanthine oxidase (and catalase), form the catalase-hydrogen peroxide complex and oxidize ethanol to acetaldehyde therein.

As used herein, and for the purpose of description, the term "ethanol-responsive active area" encompasses any and all separate active areas that are used in concert for detecting ethanol, as described herein, unless otherwise indicated. For example, the term "ethanol-responsive active area" includes both a first and second active area, such as those described with reference to FIG. 5B.

According to some embodiments, the catalase in the at least one ethanol-responsive active area of the analyte sensors described herein is not covalently bonded to the polymer. The catalase may be present in an amount ranging from about 1% to about 50% by weight of the active area polymer, more particularly from about 1% to about 10% by weight of the active area polymer, or from about 1% to about 5% by weight of the active area polymer.

The glucose-responsive active areas in the analyte sensors disclosed herein may comprise a glucose-responsive enzyme, such as glucose oxidase or glucose dehydrogenase, and a polymer. The glucose oxidase may be covalently bound to a polymer within the glucose-responsive active area, according to various embodiments. Suitable polymers for inclusion in the active areas are described below. Further, an immobilized or chemically bonded electron transfer agent (e.g., an osmium complex or other transition metal complex) may preferably be present within the glucose-responsive active area for exchanging electrons with the glucose-responsive enzyme to facilitate the formation of gluconolactone to determine glucose levels.

The glucose-responsive enzyme may be present in an amount in the range of about 1% to about 50% by weight of the polymer in the glucose-responsive active area, encompassing any value and subset therebetween, such as about 5% to about 45%, or about 10% to about 40%, or about 15% to about 35%, or about 20% to about 30% by weight of the polymer in the glucose-responsive active area. The optional electron transfer agent may be present in an amount in the range of about 10% to about 50% by weight of the polymer in the glucose-responsive active area, encompassing any value and subset therebetween, such as about 15% to about 45%, or about 20% to about 40%, or about 25% to about 35% by weight of the polymer in the glucose-responsive active area. These ranges are equally applicable to all embodiments pertaining to the glucose-responsive active areas described herein, without limitation.

As described above, analyte sensors comprising one or more glucose-responsive active areas and one or more ethanol-responsive active areas may be disposed upon a single working electrode or two or more separate working electrodes. Moreover, various membrane configurations may be possible, particularly when a selected concerted enzymatic reaction system requires separation of various components by use of a dual-layer membrane, as described above (see FIG. 5B).

Figure 6A:
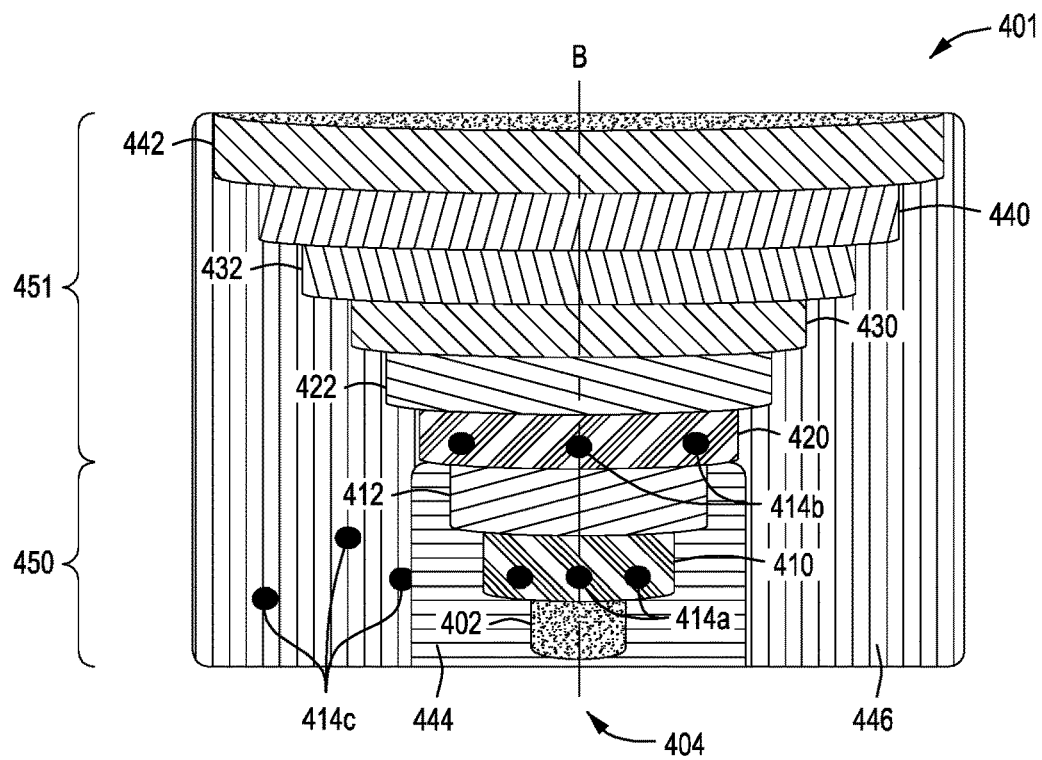
FIGS. 6A and 6B show perspective views of analyte sensors featuring cylindrical electrodes that are disposed concentrically with respect to one another and membrane configurations for detecting glucose and ethanol, according to one or more embodiments of the present disclosure.
Figure 6B:
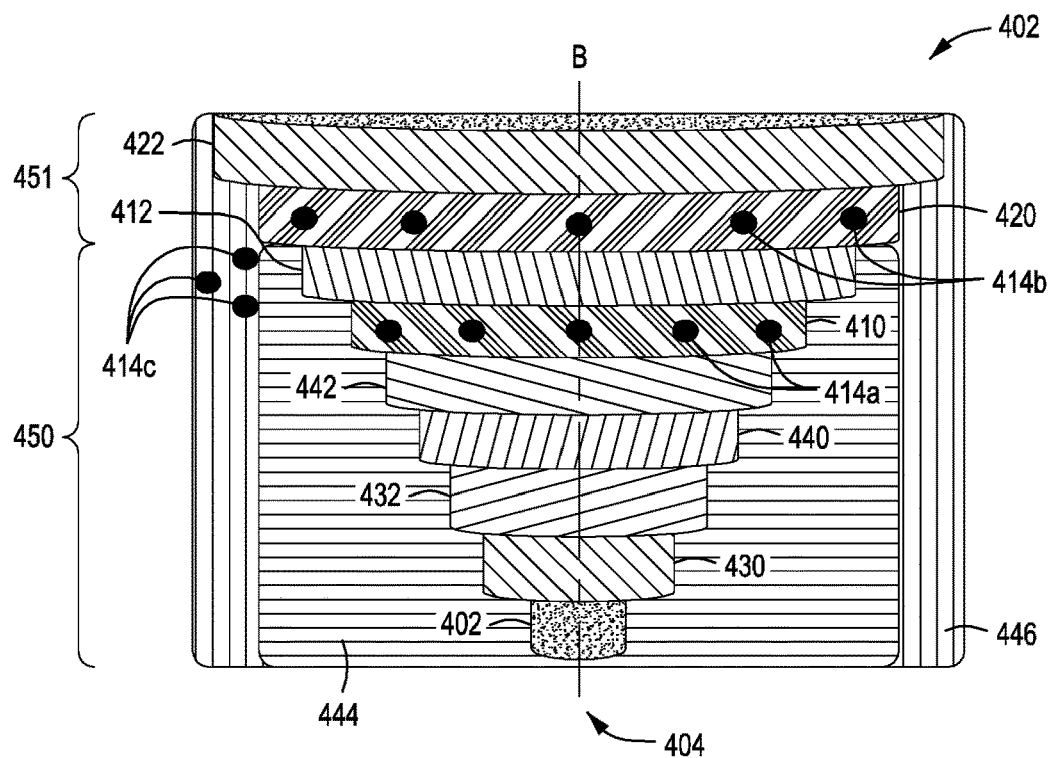
Figure 7:
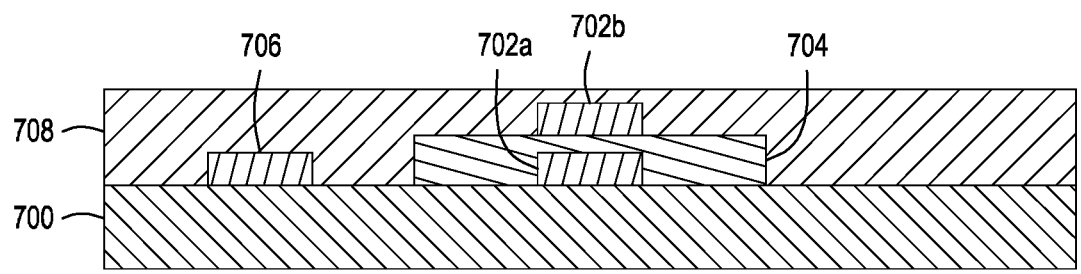
FIG. 7 shows an illustrative working electrode and membrane configuration for detecting glucose and ethanol, according to one or more embodiments of the present disclosure.

FIGS. 6A and 6B show perspective views of the illustrative sensor configuration of FIG. 4 (and like reference characters are used) comprising active areas on separate working electrodes and membrane configurations suitable for one or more of the dual glucose and ethanol sensors described herein. FIG. 7 shows a cross-sectional view of an illustrative sensor configuration comprising active areas on a single working electrode and a membrane configuration suitable for one or more of the dual glucose and ethanol sensors described herein.

Referring first to FIG. 6A, sensor 401 comprises working electrode 410, active area 414a, and dielectric layer 412 that are each overcoated with dual-layer membrane 450. Sensor 401 further comprises working electrode 420, active area 414b, active area 414c, and the remainder of the sensor tail (i.e., counter electrode 430, reference electrode 440, and dielectric layers 422, 432 and 442) that are each overcoated with single-layer membrane 451. Dual-layer membrane 450 comprises membrane layer 444 overcoated with membrane layer 446; single-layer membrane 451 comprises membrane layer 446. Dual-layer membrane 450 and single-layer membrane 451 may be of the same or different composition, as discussed in greater detail herein, and are dual-layer or single-layer with reference to at least one working electrode and the associated number of active areas required for detecting an analyte of interest.

The sensor configuration of FIG. 6A may feature active area 414b that is glucose-responsive, and first and second active areas 414a and 414c that are collectively ethanol-responsive, as described herein. Glucose-responsive active area 414b may comprise at least a glucose-responsive enzyme, a polymer, and an optional electron transfer agent. Typically, the glucose-responsive area includes the electron transfer agent.

First active area 414a may be disposed upon a surface of working electrode 410 and comprise at least xanthine oxidase, a first polymer, and an optional electron transfer agent; second active area 414c may comprise glucose oxidase, catalase, and a second polymer.

It is to be understood that although FIGS. 6A and 6B are described in which first active area 414a comprises the xanthine oxidase chemistry of FIG. 5B and second active area 414b comprises the glucose oxidase chemistry of FIG. 5B, the reverse may also be employed, as described above. That is, the specific location of the two active areas relative to the membrane (and the inclusion of catalase) is non-limiting and FIGS. 6A and 6B are merely illustrative of two configurations.

The xanthine oxidase may be present in an amount in the range of about 1% to about 50% by weight of the first polymer in the first active area 414a, encompassing any value and subset therebetween such as about 5% to about 45%, or about 10% to about 40%, or about 15% to about 35%, or about 20% to about 30% by weight of the first polymer in the first active area 414a. The optional electron transfer agent may be present in an amount in the range of about 10% to about 50% by weight of the first polymer in the first active area 414a, encompassing any value and subset therebetween, such as about 15% to about 45%, or about 20% to about 40%, or about 25% to about 35% by weight of the first polymer in the first active area 414a. The glucose oxidase may be present in an amount in the range of about 1% to about 50% by weight of the second polymer in the second active area 414c, encompassing any value and subset therebetween, such as about 5% to about 45%, or about 10% to about 40%, or about 15% to about 35%, or about 20% to about 30% by weight of the second polymer in the second active area 414c. The catalase may be present in the second active area 414c in an amount described hereinabove. It is to be appreciated that while these ranges are described with reference to FIG. 6A, they are equally applicable to all embodiments pertaining to the first and second ethanol-responsive active areas (first and second portion of the ethanol-responsive active area) described herein, without limitation.

Typically, the first active area 414a includes the electron transfer agent, and may optionally also comprise catalase (e.g., in an amount within the range disclosed herein). The first and second polymer may be of the same or different composition, and are described in greater detail herein. The second active area 414c may be disposed upon a surface of the membrane 444, bonded to membrane 446 (e.g., chemically bonded, such as covalently bonded), or otherwise immobilized within membrane 446 (e.g., unbound in the matrix of membrane 446). In preferred embodiments, the second active area 414c is deposited (e.g., chemically bonded, such as covalently bonded) upon a surface of membrane 444, or the second active area 414c is disposed outside of membrane 444 and is mobilized within membrane 446 so long as the second active area 414c is in relative close proximity to the first active area 414a to facilitate ethanol detection. The number, size, and shape of each of active areas 414a, 414b, and 414c is not limited to the number depicted in any of the figures of the present disclosure, and may be a single active area or multiple active area of various sizes and shapes, provided that they are functional to detect their particular analyte of interest. Additionally, in some embodiments, the xanthine oxidase and the electron transfer agent are covalently bonded to the first polymer of first active area 414a, and the glucose oxidase is covalently bonded to the second polymer of second active area 414c.

Still referring to FIG. 6A, although dual-layer membrane 450 and single layer membrane 451 collectively overcoat all components of the sensor tail, it is to be appreciated that other membrane configurations may be employed, without departing from the scope of the present disclosure. For example, a dual-layer membrane may overcoat only working electrode 410, active area 414a, and active area 414c; and a separate single-layer membrane may overcoat only working electrode 420 and active area 414b. Membrane coating of the remaining components of an analyte sensor described herein (e.g., counter electrode(s), reference electrode(s), dielectric layer(s)) is optional, but may be overcoated to facilitate or simplify manufacturing of the analyte sensor (e.g., simplify dip coating the membrane upon the sensor tail). Moreover, it is further to be appreciated that the positions of the various working, counter, and reference electrodes are not limited to those depicted in FIG. 6A. Similarly, the number of such electrodes is not limited to that depicted in FIG. 6A (e.g., rather than separate counter and reference electrodes, a single counter/reference electrode may be utilized).

FIG. 6B illustrates a representative alternative sensor configuration compared to FIG. 6A, in which sensor 402 contains counter electrode 430 and reference electrode 440 that are located more proximal to sensor tip 404 and working electrodes 410 and 420 that are located more distal from sensor tip 404. Sensor configurations in which working electrodes 410 and 420 are located more distal from sensor tip 404 may be advantageous by providing a larger surface area for deposition of active areas 414a and 414b (five discrete sensing spots illustratively shown in FIG. 5B, but more or less may be included), thereby facilitating an increased signal strength in some cases. The locations of the dual-layer membrane defined by membrane 450 and the single-layer membrane defined by membrane 451 have been similarly adjusted to accommodate the change in location of working electrodes 410 and 420, and the location of second active area 414c forming the concerted enzymatic reaction system with active area 414a for detecting ethanol.

Although FIGS. 5A and 5B have depicted sensor configurations that are each supported upon central substrate 402, it is to be appreciated that alternative sensor configurations may be electrode-supported instead and lack central substrate 402. In a representative embodiment, the innermost concentric electrode may be utilized to support the other electrodes and dielectric layers. For example, the sensor 402 may exclude substrate 402 and innermost concentric counter electrode 430 may be employed for disposing the reference electrode 440, working electrodes 410 and 420, and dielectric layers 432, 442, 412, and 422 sequentially thereon. In view of the disclosure herein, it is again to be appreciated that other electrode and dielectric layer configurations may be employed in sensor configurations lacking central substrate 402, and may be employed in different positional configurations.

Referring now to FIG. 7, illustrated a cross-sectional view of a portion of an illustrative sensor configuration comprising active areas on a single working electrode and a membrane configuration suitable for one or more of the dual glucose and ethanol sensors described herein. As shown, working electrode 700 comprises a glucose-responsive active area 706 and a first ethanol-responsive active area 702a disposed thereon. Glucose-responsive active area 706 may comprise a glucose-responsive enzyme and a first polymer, the glucose-responsive enzyme may be chemically (e.g., covalently) bound to the first polymer. Typically, an electron transfer agent is also present in active area 706, which also may be chemically (e.g., covalently) bound to the first polymer.

With continued reference to FIG. 7, the first ethanol-responsive active area 702a disposed upon working electrode 700 may comprise xanthine oxidase and a second polymer, the xanthine oxidase may be chemically (e.g., covalently) bound to the second polymer. Typically, an electron transfer agent is also present in active area 702a, which also may be chemically (e.g., covalently) bound to the second polymer. A first membrane 704 overcoats active area 702a in order to isolate 702a from the second ethanol-responsive active area 702b to preclude electron exchange therebetween, as described above. As depicted, the first membrane 704 may also overcoat a surface of working electrode 700, as depicted, as well as other portions of an analyte sensor in which working electrode 700 is present. Alternatively, membrane 704 may coat only active area 702a. The first membrane 704 may be at least permeable to acetaldehyde.

Second active area 702b is disposed upon membrane 704 (although in some embodiments may be bound to membrane 708, mobilized or otherwise immobilized in membrane 708), and may be chemically (e.g., covalently) bound thereto. Second active area 702b operates in concert with active area 702a, as described above, to detect in vivo ethanol levels, and may comprise glucose oxidase, catalase, and a third polymer. The glucose oxidase may be chemically (e.g., covalently) bound to the third polymer and the catalase may be chemically bound or unbound to the third polymer. The first membrane 704 further isolates the glucose oxidase, particularly when chemically bound to the third polymer, from contacting working electrode 700, thereby preventing it from generating current, such as by interaction with the electron transfer agent located within active area 702a.

As shown, the glucose-responsive active area 706 and the second ethanol-responsive active area 702b are collectively overcoated with a second membrane 708. Accordingly, a dual-layer membrane comprising membranes 704 and 708 overcoats first ethanol-responsive active area 702a, and a single-layer membrane comprising membrane 708 overcoats both glucose-responsive active area 706 and second ethanol-responsive active area 702b. Membrane 708 may additionally overcoat a surface of working electrode 700, as shown, as well as other portions of an analyte sensor in which working electrode 700 is present. Alternatively, membrane 708 may coat only active areas 706 and 702b. The second membrane 708 is at least permeable to both glucose and ethanol. Still alternatively, membrane 708 may not be continuous (i.e., are discontiguous), but separately overcoat active areas 706 and 702b, without departing from the scope of the present disclosure.

The first, second, and third polymers of active areas 706, 702a, 702b may be the same or different; similarly, the first and second membranes 704, 708 may be the same or different.

Figure 8:
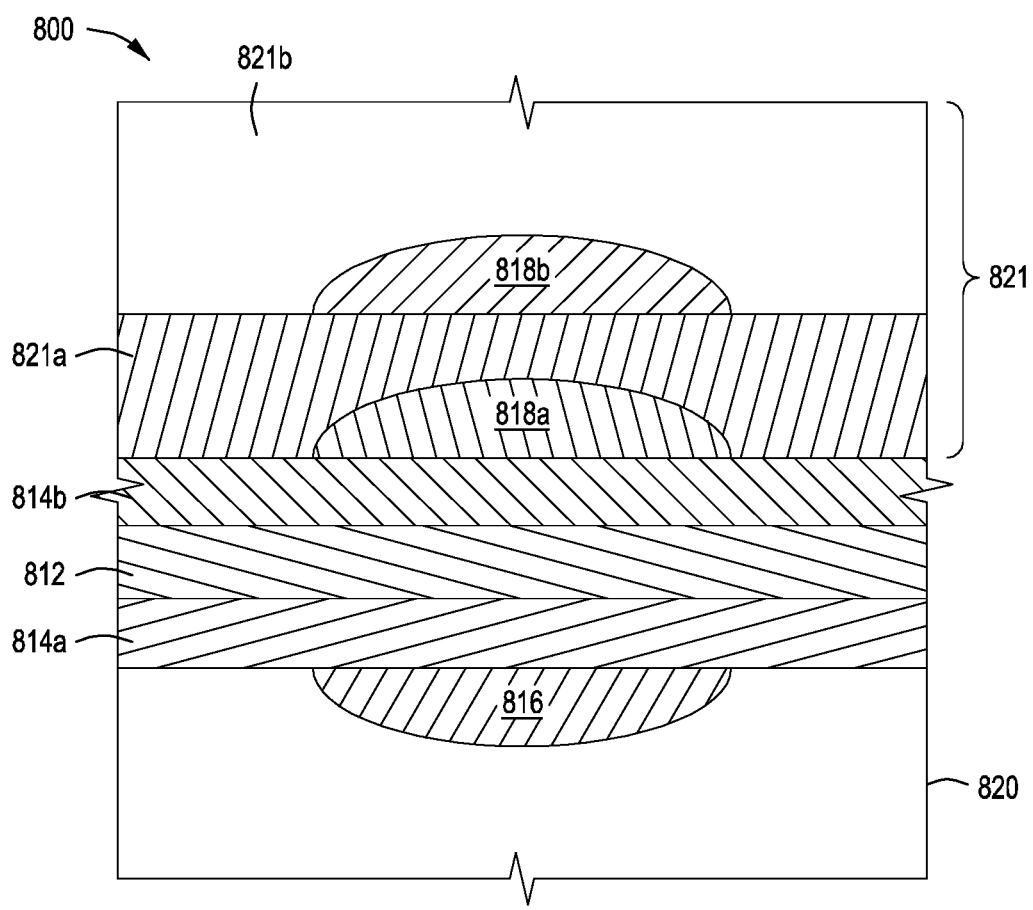
FIG. 8 shows an illustrative schematic of a portion of an analyte sensor having two working electrodes and featuring a dual-layer membrane overcoating one of the two working electrodes, which is compatible for use in some embodiments of the disclosure herein.

FIG. 8 shows an additional illustrative schematic of a portion of an analyte sensor having two working electrodes and featuring a dual-layer membrane overcoating one of the two working electrodes, which is compatible for use in forming the analyte sensors according to one or more embodiments described herein. As shown in FIG. 8, the analyte sensor features sensor tail 800 having working electrodes 814a and 814b disposed on opposite faces of substrate 812. Glucose-responsive active area 816 is disposed on a face of working electrode 814a, and a first ethanol-responsive active area (first portion of the total ethanol-responsive active area) 818a is disposed on a face of working electrode 814b. Glucose-responsive active area 816 corresponds to glucose-responsive area 706 of FIG. 7. First ethanol-responsive active area 818a corresponds to first ethanol active area 702a of FIG. 7. Although FIG. 8 has shown active areas 816 and 818a disposed generally opposite on another with respect to substrate 812, it is to be appreciate that active areas 816 and 818a may be laterally spaced apart (offset) from one another upon opposite faces of substrate 812, without departing from the scope of the present disclosure. Laterally spaced-apart configurations for active areas 818 and 818a may be particularly advantageous for overcoating each active with mass transport limiting membranes, as discussed hereinafter.

As further shown in FIG. 8, active area 816 is overcoated with single-layer membrane 820. Membrane 820 is a homogenous membrane comprising a single membrane polymer. Active area 818a is overcoated with dual-layer membrane 821, which comprises membrane layer 821a in direct contact with active area 818a and membrane layer 821b overlaying membrane layer 821a. In this embodiment, membrane layers 821a and 821b comprise different membrane polymers. In certain specific embodiments, membrane layer 820 and membrane layer 821b may comprise the same membrane polymer. A second ethanol-responsive active area disposed upon membrane layer 821a (second portion of the total ethanol-responsive active area) 818b is disposed on membrane 821a. Second ethanol-responsive active area 818b corresponds to first ethanol active area 702b of FIG. 7. First and second ethanol-responsive active areas 818a, 818b operate in concert to detect ethanol, as described herein.

In the depicted analyte sensor configuration, membrane 820 exhibits permeability for glucose, whereas membrane 821a exhibits permeability for acetaldehyde. Because second ethanol-responsive active area 818b and glucose-responsive active area 816 are both dependent upon glucose, membranes 821b and 820 may constitute the same polymer. Furthermore, active area 818a may be located more distally relative to the tip of a sensor tail such that it may be dipcoated with membrane 818a without contacting active area 816. Thereafter, active area 818b may be deposited and all of the outer portion of membrane 821a, active area 818b, and active area 816 dipcoated for deposit membrane 820. Such a configuration may facilitate manufacturing of the analyte sensor.

In some embodiments, and as described in more detail below, membrane 821a comprises a polyvinylpyridine homopolymer or copolymer and membrane 821b, 820 comprises a polyvinylpyridine-co-styrene.

According to various embodiments of the present disclosure, an electron transfer agent may be present in the glucose-responsive active area and the ethanol-responsive active area of the analyte sensors described herein. When separate active areas are utilized for ethanol detection, the electron transfer agent may be present in the active area disposed upon the working electrode (and further comprising xanthine oxidase and a polymer). Suitable electron transfer agents may facilitate conveyance of electrons to an adjacent working electrode after either analyte (glucose or ethanol), or a product thereof (acetaldehyde) undergoes an oxidation-reduction reaction, thereby generating a current that is indicative of the presence of that particular analyte. The amount of current generated is proportional to the quantity of analyte that is present. Depending on the sensor configuration used, the electron transfer agents in the glucose-responsive active area and the ethanol-responsive active area may be the same or different. The electron transfer agents may be different, for example, such that each electron transfer agent exhibits different oxidation-reduction potentials.

Suitable electron transfer agents may include electroreducible and electrooxidizable ions, complexes, or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl(imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere. In some embodiments, the selected electron transfer agent for use in the glucose-responsive and ethanol-responsive active areas described herein is an osmium complex.

Active areas suitable for detecting glucose and ethanol may also comprise a polymer to which the electron transfer agent may be covalently bound. Any of the electron transfer agents disclosed herein may comprise suitable functionality to promote covalent bonding to the polymer within the active areas. Suitable examples of electron transfer agents and polymer-bound electron transfer agents may include those described in U.S. Pat. Nos. 8,444,834, 8,268,143 and 6,605,201, the disclosures of which are incorporated herein by reference in their entirety. Examples of suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. The polymer within each area may be the same or different.

The manner of covalent bonding between the electron transfer agent and the polymer in each active area is not considered to be particularly limiting. Covalent bonding may take place by polymerizing a monomer unit bearing a covalently bound electron transfer agent, or the electron transfer agent may be reacted with the polymer separately after the polymer has already been synthesized. According to some embodiments, a bifunctional spacer may covalently bond the electron transfer agent to the polymer within an active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, according to some or other various embodiments of the present disclosure, the enzyme within one or more of the active areas may be covalently bonded to the polymer. When multiple enzymes are present in a single active area, all of the multiple enzymes may be covalently bonded to the polymer in some embodiments, and in other embodiments, only a portion of the multiple enzymes may be covalently bonded to the polymer. For example, one or more enzymes comprising a concerted enzymatic reaction system may be covalently bonded to the polymer and at least one enzyme may be non-covalently associated with the polymer, such that the non-covalently bonded enzyme is physically entrained within the polymer (e.g., in some embodiments, glucose oxidase is covalently bonded and catalase is non-covalently bonded in an ethanol-responsive active area). According to certain embodiments, covalent bonding of the enzyme(s) to the polymer in an active area may take place via a crosslinker introduced with a suitable crosslinking agent. Suitable crosslinking agents for reaction with free amino groups in the enzyme (e.g., with the free side chain amine in lysine) may include crosslinking agents such as, for example, polyethylene glycol diglycidylether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking of the enzyme to the polymer is generally intermolecular, but can be intramolecular in some embodiments. Such crosslinkers may additionally be used for crosslinking the membrane polymers described herein.

The electron transfer agent and/or the enzyme(s) may be associated with the polymer in the active area through means other than covalent bonding as well. In some embodiments, the electron transfer agent and/or the enzyme(s) may be ionically or coordinatively associated with the polymer. For example, a charged polymer may be ionically associated with an oppositely charged electron transfer agent or enzyme(s). In still other embodiments, the electron transfer agent and/or the enzyme(s) may be physically entrained or immobilized within the polymer without being bonded thereto.

In particular embodiments of the present disclosure, the mass transport limiting membrane overcoating each active area may comprise at least a crosslinked polyvinylpyridine homopolymer or copolymer. The composition of the mass transport limiting membrane may be the same or different where the mass transport limiting membrane overcoats each active area. In particular embodiments, the mass transport limiting membrane overcoating the glucose-responsive active area and may be a single-layer membrane (and containing a single membrane polymer). In particular embodiments, the mass transport limiting membrane overcoating a first portion of the ethanol-responsive active area may be a dual-layer (each layer containing the same or different membrane polymer) and the mass transport limiting membrane overcoating a second portion of the ethanol-responsive active area may be a single-layer membrane, as described herein. In more specific embodiments of the present disclosure, the glucose-responsive active area may be overcoated with a membrane comprising a polyvinylpyridine-co-styrene copolymer, and the ethanol-responsive active area may be overcoated with a dual-layer membrane comprising polyvinylpyridine and polyvinylpyridine-co-styrene, wherein the polyvinylpryidine membrane overcoats the ethanol-responsive active area disposed upon the working electrode (e.g., membrane 704 of FIG. 7). One or both of the polyvinylpryidine membrane polymer and the polyvinylpyridine-co-styrene membrane polymer may be crosslinked. Further, the polyvinylpyridine-co-styrene membrane polymer may be functionalized, wherein a portion of the pyridine nitrogen atoms are functionalized with a non-crosslinked poly(ethylene glycol) tail and a portion of the pyridine nitrogen atoms are functionalized with an alkylsulfonic acid group. In some instances, the mass transport limiting membrane may reduce the flux of an analyte to a surface of an electrode (e.g., the working electrode) by a factor of about 10 to about 1000, encompassing any value and subset therebetween.

In light of the foregoing, various embodiments of a stand-alone ethanol sensor are disclosed herein. Further, dual glucose-responsive and ethanol-responsive sensor sensors are disclosed herein. Such dual glucose-responsive and ethanol-responsive sensors allow concurrent, but separate detection of each analyte. That is, the glucose-responsive active area and the ethanol-responsive active area(s) are arranged in a single analyte sensor such that they can be interrogated separately to facilitate detection of each analyte. That is, the glucose-responsive active area and the ethanol-responsive active area(s) each produce independent signals representative of analyte levels (concentration). For example, in some embodiments, signals associated with the enzymatic reaction occurring within each of the glucose-responsive active area and the ethanol-responsive active area may be measured separately by interrogating each active area and/or working electrode at the same time or at different times. The signal associated with each active area may then be correlated to the concentration of each of glucose and ethanol, respectively.

In some embodiments wherein the glucose-responsive active area and the ethanol-responsive active area are arranged upon a single working electrode, the oxidation-reduction potential associated with the glucose-responsive active area may be separated from the oxidation-reduction potential of the ethanol-responsive active area by at least about 100 mV, or by at least about 150 mV, or by at least about 200 mV. The upper limit of the separation between the oxidation-reduction potentials is dictated by the working electrochemical window in vivo. By having the oxidation-reduction potentials of the two active areas sufficiently separated in magnitude from one another, an electrochemical reaction may take place within one of the two active areas (i.e., within the glucose-responsive active area or the ethanol-responsive active area) without substantially inducing an electrochemical reaction within the other active area. Thus, a signal from one of the glucose-responsive active area or the ethanol-responsive active area may be independently produced at or above its corresponding oxidation-reduction potential (the lower oxidation-reduction potential) but below the oxidation-reduction potential of the other of the glucose-responsive active area and the ethanol-responsive active area (the higher oxidation-reduction potential).

At or above the oxidation-reduction potential (the higher oxidation-reduction potential) of the other active area that was not previously interrogated, in contrast, electrochemical reactions may occur within both the glucose-responsive active area and the ethanol-responsive active area. As such, the resulting signal at or above the higher oxidation-reduction potential may include a signal contribution from both the glucose-responsive active area and the ethanol-responsive active area, and the observed signal is a composite signal. The signal contribution from one active area (either the glucose-responsive active area or the ethanol-responsive active area) at or above its oxidation-reduction potential may then be determined by subtracting from the composite signal the signal obtained solely from either the glucose-responsive active area or the ethanol-responsive active area at or above its corresponding oxidation-reduction potential.

In more specific embodiments, the glucose-responsive active area and the ethanol-responsive active area may contain different electron transfer agents when the active areas are located upon the same working electrode, so as to afford oxidation-reduction potentials that are sufficiently separated in magnitude from one another. More specifically, the glucose-responsive active area may comprise a first electron transfer agent and the ethanol-responsive active area may comprise a second electron transfer agent, with the first and second electron transfer agents being different. The metal center and/or the ligands present in a given electron transfer agent may be varied to provide sufficient separation of the oxidation-reduction potentials within the two active areas, according to various embodiments of the present disclosure.

Ideally, glucose-responsive active areas and ethanol-responsive active areas located upon a single working electrode may be configured to attain a steady state current rapidly upon operating the analyte sensor at a given potential. Rapid attainment of a steady state current may be promoted by choosing an electron transfer agent for each active area that changes its oxidation state quickly upon being exposed to a potential at or above its oxidation-reduction potential. Making the active areas as thin as possible may also facilitate rapid attainment of a steady state current. For example, suitable thicknesses for the glucose-responsive active area and ethanol-responsive active area may range from about 0.1 micrometers (pm) to about 10 µm, encompassing any value and subset therebetween. In some or other embodiments, combining a conductive material such as, for example, carbon nanotubes, graphene, or metal nanoparticles within one or more of the active areas may promote rapid attainment of a steady state current. Suitable amounts of conductive particles may range from about 0.1% to about 50% by weight of the active area, or from about 1% to about 50% by weight, or from about 0.1% to about 10% by weight, or from about 1% to about 10% by weight, encompassing any value and subset therebetween. Stabilizers may also be employed to promote response stability, such as catalase, as described above.

It is also to be appreciated that the sensitivity (output current) of the analyte sensors toward each analyte may be varied by changing the coverage (area or size) of the active areas, the areal ratio of the active areas with respect to one another, the identity, thickness, and/or composition of a mass transport limiting membrane overcoating the active areas. Variation of these parameters may be conducted readily by one having ordinary skill in the art once granted the benefit of the disclosure herein.

In some embodiments, the signals associated with each active area may be correlated to a corresponding concentration of glucose or ethanol by consulting a lookup table or calibration curve for each analyte. A lookup table for each analyte may be populated by assaying multiple samples having known analyte concentrations and recording the sensor response at each concentration for each analyte. Similarly, a calibration curve for each analyte may be determined by plotting the analyte sensor response for each analyte as a function of the concentration and determining a suitable calibration function over the calibration range (e.g., by regression, particularly linear regression).

A processor may determine which sensor response value in a lookup table is closest to that measured for a sample having an unknown analyte concentration and then report the analyte concentration accordingly. In some or other embodiments, if the sensor response value for a sample having an unknown analyte concentration is between the recorded values in the lookup table, the processor may interpolate between two lookup table values to estimate the analyte concentration. Interpolation may assume a linear concentration variation between the two values reported in the lookup table. Interpolation may be employed when the sensor response differs a sufficient amount from a given value in the lookup table, such as by variation of about 10% or greater.

Likewise, according to some or other various embodiments, a processor may input the sensor response value for a sample having an unknown analyte concentration into a corresponding calibration function. The processor may then report the analyte concentration accordingly.

Accordingly, the present disclosure provides for an analyte sensor comprising a sensor tail and at least one working electrode. A glucose-responsive active area is disposed upon a surface of the working electrode and a first portion of an ethanol-responsive active area is disposed upon a surface of the working electrode, the glucose-responsive active area and first portion of the ethanol-responsive active area being spaced apart (e.g., laterally or on opposite sides of the working electrode). The glucose-responsive active area comprises a glucose-responsive enzyme and an optional electron transfer agent. The glucose-responsive active area additionally comprises a polymer. The first portion of the ethanol-responsive active area comprises xanthine oxidase, a first polymer, and an optional electron transfer agent. The first portion of the ethanol-responsive active area may further comprise a stabilizer, such as catalase. A first membrane is disposed only upon the first portion of the ethanol-responsive active area (as well as optionally a surface of the working electrode adjacent thereto, the first membrane comprising a first membrane polymer and being permeable to at least acetaldehyde. A second portion of the ethanol-responsive active area is disposed upon the first membrane, the second portion of the ethanol-responsive active area comprising glucose oxidase, catalase, and a second polymer. A second membrane is disposed upon the glucose-responsive active area and the second portion of the ethanol-responsive active area, the second membrane comprising a second membrane polymer and being permeable to at least glucose and ethanol. The glucose oxidase present in the glucose-responsive active area is capable of generating a signal at the working electrode proportional to a glucose concentration and the xanthine oxidase and glucose oxidase of the first and second portion of the ethanol-responsive active area are capable of interacting in concert to generate a signal at the working electrode proportional to an ethanol concentration.

In some embodiments, the first and second membrane may be one of a polyvinylpyridine (e.g., poly(4-vinylpyridine)), a polyvinylimidazole (e.g., poly(1-vinylimidazole)), or any copolymer thereof. The first and second membrane polymer may comprise polyvinylpryidine. In some embodiments, the first membrane is polyvinylpyridine and the second membrane polymer is polyvinylpyridine-co-styrene. In some embodiments, the first membrane polymer is cross-linked polyvinylpyridine, which is readily permeable to acetaldehyde; and the second membrane polymer is a cross-linked polyvinylpyridine-co-styrene polymer, in which a portion of the pyridine nitrogen atoms are functionalized with a non-crosslinked poly(ethylene glycol) tail and a portion of the pyridine nitrogen atoms are functionalized with an alkylsulfonic acid group, which is readily permeable to both glucose and ethanol.

In some embodiments, one or both of the glucose-responsive active area and the first portion of the ethanol-responsive reactive area comprises the electron transfer agent. In some embodiments, the included electron transfer agent is a transition metal complex, such as an osmium complex.

Various components of the active areas may further be covalently bound therein. For example, in some embodiments, the glucose-oxidase is covalently bound to a polymer in the glucose-responsive active area; the xanthine oxidase and the optional electron transfer agent are covalently bound to the first polymer in the first portion of the ethanol-responsive active area; and the glucose oxidase is covalently bound to the second polymer in the second portion of the ethanol-responsive active area. The catalase in the first or second portion of the ethanol-responsive active area may be covalently bound or un-bound. In some embodiments, the catalase is un-bound to the first or second portion of the ethanol-responsive active area and instead physically constrained within or adjacent to the first or second portion by any of the first polymer, the second polymer, the first membrane, and/or the second membrane.

In some embodiments, the analyte sensor may comprise two working electrodes, where the glucose-responsive active area is on a first working electrode and the first and second portion of the ethanol-responsive area is on a second working electrode, and otherwise having the composition and membrane configuration described above.

The sensor tail of the analyte sensor is configured for insertion into a tissue, such as such as dermally, subcutaneously, or intravenously so that analyses may be conducted in vivo. Accordingly, the present disclosure provides a method of sensing glucose and ethanol using the analyte sensor described above (comprising one or more working electrodes). In particular, the analyte sensor is exposed to a body fluid comprising at least one of glucose and ethanol. That is, during the duration of a user wearing an on-body unit comprising the analyte sensor (e.g., one day or more, such as up to about one month), the body fluid is expected to comprise at least one of glucose and ethanol. A first signal and a second signal are detected (e.g., by electrochemical detection) from the analyte sensor glucose-responsive active area and ethanol-responsive active area (comprising the first and second portion thereof), respectively. The first signal is proportional to a concentration of glucose and the second signal is proportional to a concentration of ethanol.

In some embodiments, the detection of the glucose and ethanol from the analyte sensors described above is based on varying oxidation-reduction potentials between the glucose-responsive active area and the ethanol-responsive active area, particularly when the analyte sensor comprises a single working electrode, although also applicable to analyte sensors comprising more than one working electrode. The analyte sensor is exposed to a body fluid comprising at least one of glucose and ethanol. Each of the glucose-responsive active area and the ethanol-responsive active area (comprising the first and second portion thereof) has an oxidation-reduction potential that are sufficiently separated to allow independent detection of a first signal from the glucose-responsive active area and a second signal from the ethanol-responsive active area. In some embodiments, a first signal is detected at or above a lower of the oxidation-reduction potential and the second oxidation-reduction potential but below a higher of the first oxidation-reduction potential and the second oxidation-reduction potential, such that the first signal is proportional to a concentration of one of glucose or ethanol in the body fluid. A second signal is detected at or above a higher of the first oxidation-reduction potential and the second oxidation-reduction potential, such that the second signal is a composite signal comprising a signal contribution from both the glucose-responsive active area and a signal contribution from the ethanol-responsive active area. Thereafter, the first signal is subtracted from the second signal to obtain a difference signal, the difference signal being proportional to a concentration of one of glucose and ethanol.

Embodiments Disclosed Herein Include:

Embodiment A: An analyte sensor comprising: a sensor tail comprising at least a working electrode; a glucose-responsive active area disposed upon a surface of the working electrode, the glucose-responsive active area comprising a glucose-responsive active enzyme; a first portion of an ethanol-responsive active area disposed upon a surface of the working electrode spaced apart from the glucose-responsive active area, the first portion of the ethanol-responsive active area comprising xanthine oxidase, a first polymer, and an optional electron transfer agent; a first membrane disposed upon the first portion of the ethanol-responsive active area, the first membrane comprising a first membrane polymer and being permeable to at least acetaldehyde; a second portion of the ethanol-responsive active area disposed upon the first membrane, the second portion of ethanol-responsive active area comprising glucose-oxidase, catalase, and a second polymer; and a second membrane disposed upon the glucose-responsive active area and the second portion of the ethanol-responsive active area, the second membrane comprising a second membrane polymer and being permeable to at least glucose and ethanol.

Embodiment B: An analyte sensor comprising: a sensor tail comprising at least a first working electrode and a second working electrode; a glucose-responsive active area disposed upon a surface of the first working electrode, the glucose-responsive active area comprising a glucose-responsive active enzyme; a first portion of an ethanol-responsive active area disposed upon a surface of the second working electrode, the first portion of the ethanol-responsive active area comprising xanthine oxidase, a first polymer, and an optional electron transfer agent; a first membrane disposed upon the first portion of the ethanol-responsive active area, the first membrane comprising a first membrane polymer and being permeable to at least acetaldehyde; a second portion of the ethanol-responsive active area disposed upon the first membrane, the second portion of ethanol-responsive active area comprising glucose-oxidase, catalase, and a second polymer; and a second membrane disposed upon the glucose-responsive active area and the second portion of the ethanol-responsive active area, the second membrane comprising a second membrane polymer and being permeable to at least glucose and ethanol.

Embodiment C: A method comprising: exposing an analyte sensor to a body fluid comprising at least one of glucose and ethanol, the analyte sensor comprising: a sensor tail comprising at least a working electrode; a glucose-responsive active area disposed upon a surface of the working electrode, the glucose-responsive active area comprising a glucose-responsive active enzyme; a first portion of an ethanol-responsive active area disposed upon a surface of the working electrode spaced apart from the glucose-responsive active area, the first portion of the ethanol-responsive active area comprising xanthine oxidase, a first polymer, and an optional electron transfer agent; a first membrane disposed upon the first portion of the ethanol-responsive active area, the first membrane comprising a first membrane polymer and being permeable to at least acetaldehyde; a second portion of the ethanol-responsive active area disposed upon the first membrane, the second portion of ethanol-responsive active area comprising glucose-oxidase, catalase, and a second polymer; and a second membrane disposed upon the glucose-responsive active area and the second portion of the ethanol-responsive active area, the second membrane comprising a second membrane polymer and being permeable to at least glucose and ethanol; and detecting a first signal proportional to a concentration of glucose and a second signal proportional to a concentration of ethanol.

Embodiment D: A method comprising: exposing an analyte sensor to a body fluid comprising at least one of glucose and ethanol, the analyte sensor comprising: a sensor tail comprising at least a first working electrode and a second working electrode; a glucose-responsive active area disposed upon a surface of the first working electrode, the glucose-responsive active area comprising a glucose-responsive active enzyme; a first portion of an ethanol-responsive active area disposed upon a surface of the second working electrode, the first portion of the ethanol-responsive active area comprising xanthine oxidase, a first polymer, and an optional electron transfer agent; a first membrane disposed upon the first portion of the ethanol-responsive active area, the first membrane comprising a first membrane polymer and being permeable to at least acetaldehyde; a second portion of the ethanol-responsive active area disposed upon the first membrane, the second portion of ethanol-responsive active area comprising glucose-oxidase, catalase, and a second polymer; and a second membrane disposed upon the glucose-responsive active area and the second portion of the ethanol-responsive active area, the second membrane comprising a second membrane polymer and being permeable to at least glucose and ethanol; and detecting a first signal proportional to a concentration of glucose and a second signal proportional to a concentration of ethanol.

Embodiment E: An analyte sensor comprising: a sensor tail comprising at least a working electrode; a glucose-responsive active area disposed upon a surface of the working electrode, the glucose-responsive active area comprising a glucose-responsive active enzyme; a first portion of an ethanol-responsive active area disposed upon a surface of the working electrode spaced apart from the glucose-responsive active area, the first portion of the ethanol-responsive active area comprising xanthine oxidase, a first polymer, and an optional electron transfer agent; a first membrane disposed upon the first portion of the ethanol-responsive active area, the first membrane comprising a first membrane polymer and being permeable to at least acetaldehyde; a second portion of the ethanol-responsive active area disposed upon the first membrane, the second portion of ethanol-responsive active area comprising glucose oxidase, catalase, and a second polymer; and a second membrane disposed at least upon the glucose-responsive active area, the second membrane comprising a second membrane polymer and being permeable to at least glucose and a third membrane disposed at least upon the ethanol-responsive active area, the third membrane comprising a third membrane polymer and permeable to at least ethanol.

Each of Embodiments A, B, C, D, and E may have one or more of the following additional elements in any combination:

Element 1: Wherein the sensor tail is configured for insertion into a tissue.

Element 2: Wherein the first and second membrane polymer are one of a polyvinylpyridine, a polyvinylimidazone, or any copolymer thereof.

Element 3: Wherein the first membrane is polyvinylpyridine and the second membrane polymer is polyvinylpyridine-co-styrene.

Element 4: Wherein the xanthine oxidase is covalently bound to the first polymer in the first portion of the ethanol-responsive active area, and the glucose oxidase is covalently bound to the second polymer in the second portion of the ethanol-responsive active area.

Element 5: Wherein the first portion of the ethanol-responsive active area comprises the electron transfer agent, and the electron transfer agent is covalently bound to the first polymer.

Element 6: Wherein the first portion of the ethanol-responsive active area comprises the electron transfer agent, the electron transfer agent is covalently bound to the first polymer, and the electron transfer agent comprises an osmium complex.

Element 7: Wherein the first portion of the ethanol-responsive active area further comprises catalase.

Element 8: Wherein the glucose-responsive enzyme is glucose oxidase or glucose dehydrogenase.

Element 9: Wherein the second membrane is discontiguous.

Element 10: Wherein the third membrane is one of a polyvinylpyridine, a polyvinylimidazone, or any copolymer thereof.

By way of non-limiting example, exemplary combinations applicable to A, B, C, and D include:

Elements 1 and 2; 1 and 3; 1 and 4; 1 and 5; 1 and 6; 1 and 7; 1 and 8; 1 and 9; 1 and 10; 2 and 3; 2 and 4; 2 and 5; 2 and 6; 2 and 7; 2 and 8; 2 and 9; 2 and 10; 3 and 4; 3 and 5; 3 and 6; 3 and 7; 3 and 8; 3 and 9; 3 and 10; 4 and 5; 4 and 6; 4 and 7; 4 and 8; 5 and 6; 5 and 7; 5 and 8; 6 and 7; 6 and 8; 7 and 8; and any non-limiting combination of one, more, or all of 1, 2, 3, 4, 5, 6, 7, and 8.

By way of non-limiting example, exemplary combinations applicable to E include:

Elements 1 and 2; 1 and 3; 1 and 4; 1 and 5; 1 and 6; 1 and 7; 1 and 8; 2 and 3; 2 and 4; 2 and 5; 2 and 6; 2 and 7; 2 and 8; 3 and 4; 3 and 5; 3 and 6; 3 and 7; 3 and 8; 4 and 5; 4 and 6; 4 and 7; 4 and 8; 4 and 9; 4 and 10; 5 and 6; 5 and 7; 5 and 8; 5 and 9; 5 and 10; 6 and 7; 6 and 8; 6 and 9; 6 and 10; 7 and 8; 7 and 9; 7 and 10; 8 and 9; 8 and 10; 9 and 10; and any non-limiting combination of one, more, or all of 1, 2, 3, 4, 5, 6, 7, 8, 9, and 10.

To facilitate a better understanding of the embodiments described herein, the following examples of various representative embodiments are given. In no way should the following examples be read to limit, or to define, the scope of the invention.

Example: Detection of Ethanol Using an Analyte Sensor Having Two Different Enzymes Operating In Concert on a Single Working Electrode (XOX/GOX). A first spotting solution having the formulation shown in Table 1 was prepared. All of the components were dissolved in 10 mM HEPES buffer at pH 8. Crosslinking was accomplished with polyethylene glycol diglycidyl ether.

TABLE 1

Xanthine Oxidase Solution

| Component | Concentration (mg/mL) |
| --- | --- |
| XOX | 25 |
| Catalase | 12 |
| PVI (pH = 5.8) | 12 |
| Os complex | 8 |
| PEGDE400 | 6 |

~15 nL of the first spotting solution was deposited on a carbon working electrode as a single spot (XOX spot) having an area of approximately 0.05 mm$^2$. Following deposition, the working electrode was cured overnight at 25° C.

After curing, a poly(4-vinylpyridine) (PVP) membrane was deposited upon the working electrode and the XOX spot from a coating solution containing 100 mg/mL PVP and 100 mg/mL PEGDE400. Membrane deposition was accomplished by dip coating the electrode three times in the coating solution. Spray coating, screen printing, or similar processes may be alternately used to deposit the membrane. Following deposition, the electrode was cured overnight at 25° C. and then further cured in desiccated vials at 56° C. for two days.

A second spotting solution having the formulation shown in Table 2 was prepared. All of the components were dissolved in 10 mM HEPES buffer at pH 8. Crosslinking was accomplished with polyethylene glycol diglycidyl ether.

TABLE 2

Glucose Oxidase Solution

| Component | Concentration (mg/mL) |
| --- | --- |
| GOX | 16 |
| Catalase | 32 |
| PVI (pH = 5.8) | 32 |
| PEGDE400 | 6 |

~15 nL of the second spotting solution was deposited on the PVP membrane from above as a single spot (GOX spot) having an area of approximately 0.05 mm$^2$. Following deposition, curing was performed overnight at 25° C.

After curing, a second membrane was deposited upon the GOX spot and the PVP membrane. The membrane polymer in this case was a crosslinked polyvinylpyridine-co-styrene polymer, in which a portion of the pyridine nitrogen atoms were functionalized with a non-crosslinked poly(ethylene glycol) tail and a portion of the pyridine nitrogen atoms were functionalized with an alkylsulfonic acid group. The membrane at this location was deposited from a coating solution comprising 35 mg/mL of the crosslinked polyvinylpyridine-co-styrene polymer and 100 mg/mL PEGDE400. Membrane deposition was accomplished by dip coating the electrode three times in the coating solution. Spray coating, screen printing, or similar processes may be alternately used to deposit the membrane. Following deposition, the electrode was cured overnight at 25° C. and then further cured in desiccated vials at 56° C. for two days.

Ethanol analyses were conducted by immersing the electrode in ethanol-containing PBS solutions each containing varying concentrations of ethanol, as well as 5 mM of glucose (which is needed to produce hydrogen peroxide). While 5 mM of glucose was included in the solutions, it is to be understood that other glucose concentrations may also be used to carry out the described example, such as about 4 mM to about 30 mM glucose. FIG. 9A shows two replicates of the response for an electrode containing glucose oxidase and xanthine oxidase layered in separate active areas and spaced apart by a membrane upon exposure to varying ethanol concentrations, in which catalase is in the active area with glucose oxidase. As shown, the current response increased over the course of several minutes following exposure to a new ethanol concentration before stabilizing thereafter. Good reproducibility between the two replicates was observed.

Figure 9B:
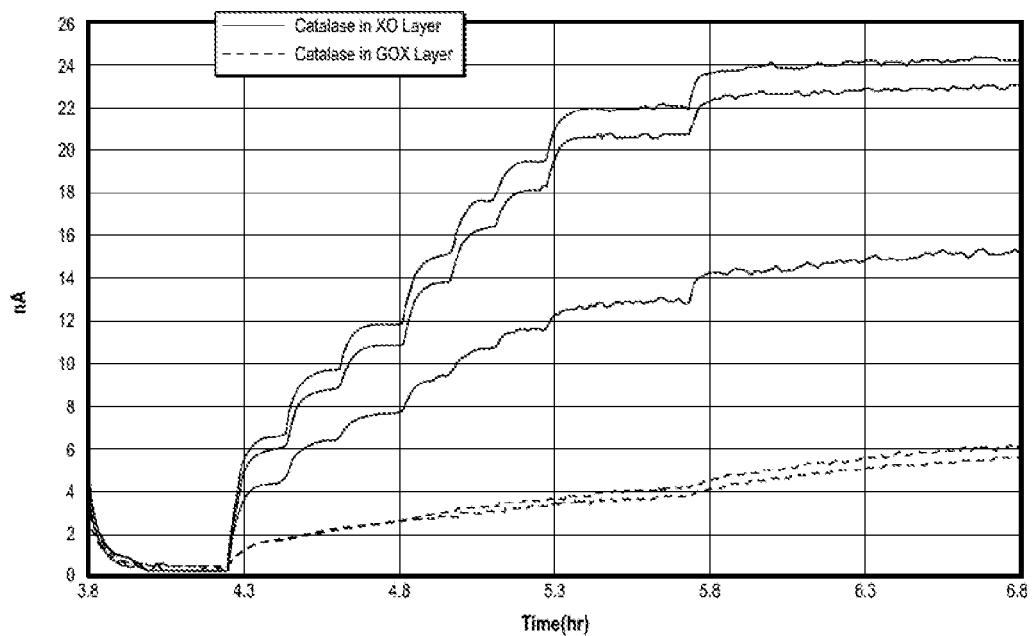
FIG. 9B shows comparative response data between an electrode containing glucose oxidase and xanthine oxidase layered in separate active areas and spaced apart by a membrane upon exposure to varying ethanol concentrations, in which catalase is present in the active areas separately.
Figure 10:
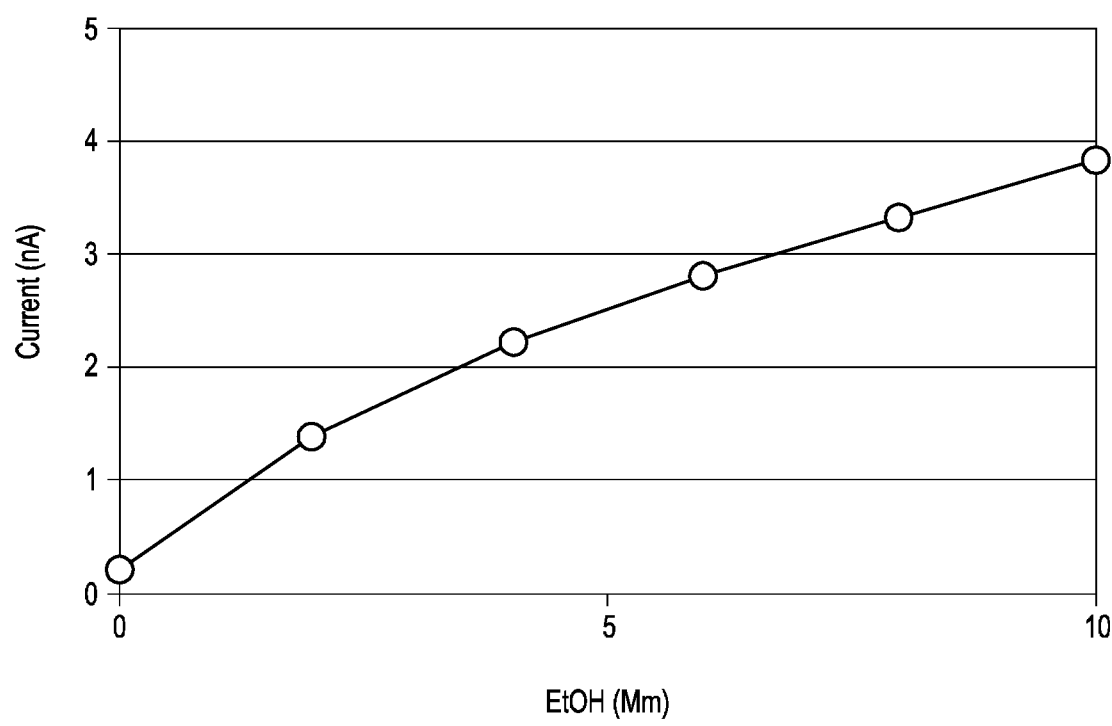
FIG. 10 shows an illustrative plot of average current response versus ethanol concentration for the electrodes of FIG. 9A.

FIG. 9B shows comparative response data between an electrode containing glucose oxidase and xanthine oxidase layered in separate active areas and spaced apart by a membrane upon exposure to varying ethanol concentrations, in which catalase is present in the active areas separately. As shown, the sensor response was greater when the catalase was included in the active area containing xanthine oxidase. FIG. 10 shows an illustrative plot of average current response versus ethanol concentration.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Analyte Sensor Ignition Lock

Vehicle fail safes, such as ignition locks, are sometimes used to prevent an operator from operating a vehicle when impaired or otherwise not in a condition to safely operate the vehicle. Operating the vehicle while impaired could potentially present significant dangers to the operator and the public. One common type of ignition lock is designed to prevent drunk driving and, more specifically, to prevent individuals from operating a vehicle while intoxicated through alcohol use. Such lock devices connect a breath-alcohol analyzer or optical sensor to the vehicle's ignition system, and the driver must successfully pass a blood alcohol level test before the vehicle can be started.

Intoxication is one type of impairment or condition that an operator may experience that renders the operator unfit or unable to operate a vehicle. However, other impairments and conditions can also afflict an operator and should also be monitored closely to ensure the operator does not operate a vehicle while impaired. For example, an operator with diabetes and driving while hypoglycemic (i.e., low blood sugar) could potentially undergo light-headedness, confusion, headache, loss of consciousness, seizures, and delayed reflexes, any of which could endanger his/her own life and those in the vehicle or in the vicinity of the vehicle.

Analyte monitoring systems, have been developed to facilitate long-term monitoring of analytes in bodily fluid (e.g., blood). Some analyte monitoring systems are designed to detect and monitor levels of blood glucose, which can be helpful in treating diabetic conditions. Other analyte monitoring systems, however, are designed to detect and monitor other analytes present in an operator's bodily fluid, and abnormal analyte levels detected in an operator may be indicative that the operator is currently unfit to safely operate a vehicle.

The following discussion describes an analyte monitoring and vehicle control system used to prevent operation of a vehicle when operator analyte levels cross a predetermined threshold. Having the sensor control device 102 (FIG. 1) properly deployed allows a user to intelligently track and monitor bodily fluid analyte levels and trends. When some analyte levels surpass certain thresholds, physical or cognitive impairment may ensue that renders a user unfit to safely operate a vehicle. In such instances, the user should take appropriate action to bring analyte levels back into safe ranges prior to attempting to operate a vehicle. In some cases, however, a user may feel perfectly fine to operate a vehicle but nonetheless have unsafe analyte levels that could suddenly trigger the onset of a dangerous physical impairment. In such cases, it may be advantageous to have a failsafe system in place that prevents or warns the user from operating a vehicle and potentially placing self and/or others in danger.

Figure 11:
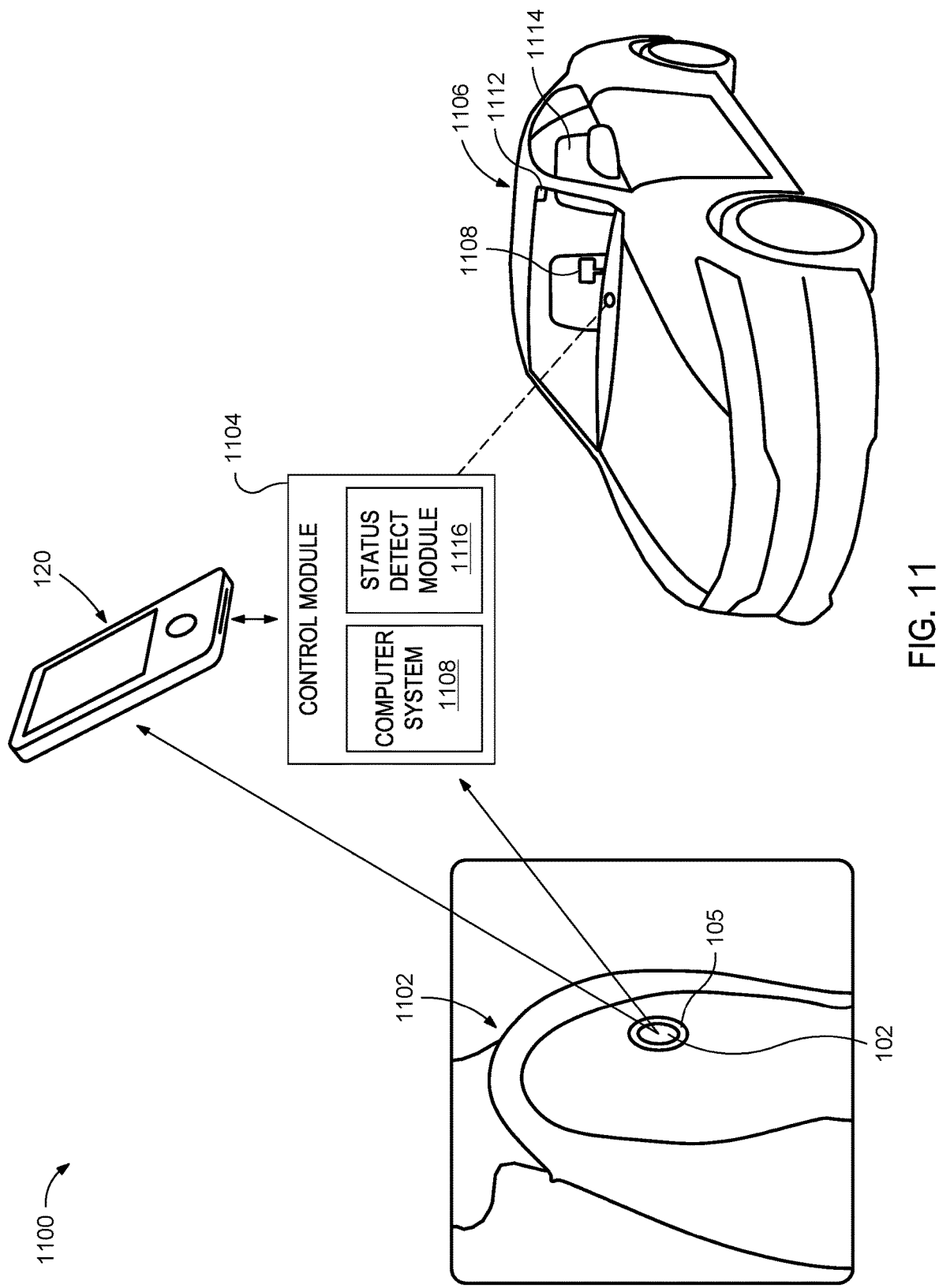
FIG. 11 is a schematic diagram of an example analyte monitoring and vehicle control system, according to one or more embodiments of the present disclosure.

FIG. 11 is a schematic diagram of an example analyte monitoring and vehicle control system 1100, according to one or more embodiments of the present disclosure. As illustrated, the analyte monitoring and vehicle control system 1100 (hereafter "the system 1100) includes the sensor control device 102, which may be deployed on a user or "operator" 3202 and otherwise delivered to a target monitoring location on the body of the operator 1102, such as the back of an arm. As discussed above, the sensor control device 102 includes the sensor 104 (FIG. 1), and when properly deployed, the sensor 104 is positioned transcutaneously within the skin to detect and monitor analytes present within a bodily fluid of the operator 1102. The adhesive patch 105 (FIG. 1) applied to the bottom of the sensor control device 102 adheres to the skin to secure the sensor control device 102 in place during operation.

While the system 1100 is described herein as including the on-body sensor control device 102 to detect and report analyte levels, the system 1100 may alternatively incorporate an ex vivo analyte sensor (e.g., a self-monitoring blood glucose "SMBG" meter), without departing from the scope of the disclosure. Accordingly, the term "sensor control device" should be interpreted herein to include not only on-body sensor systems, as generally described above, but also traditional, hand-held sensor systems.

As illustrated, the system 1100 may further include the reader device 120, and the sensor control device 102 may be in communication with the reader device 120 via a local communication path or link to provide analyte concentration data automatically, periodically, or as desired by the operator 1102. The reader device 120 may be in communication with a control module 1104, which is in communication with the electrical system of a vehicle 1106 and powered by the vehicle battery or otherwise powered by a separate battery. In such embodiments, data transmitted to the reader device 120 from the sensor control device 102 may be subsequently transmitted by the reader device 120 to the control module 1104 for processing. In other embodiments, however, the sensor control device 102 may communicate directly with the control module 1104 via any wireless communication protocol, such as BLUETOOTH®. In such embodiments, the reader device 120 may or may not be necessary in the system 1100.

In the illustrated embodiment, the vehicle 1106 is depicted as an automobile. As used herein, however, the term "vehicle" is used broadly and is meant to include any kind of transportation vehicle that can be operated by a human user or "operator," but can also include autonomous vehicles used to transport humans. Examples of the vehicle 1106 include, but are not limited to, any type of automobile, truck, sport utility vehicle, aircraft, watercraft, spacecraft, and or any other means of transportation, or combinations thereof.

The control module 1104 may include a communications interface to communicate information to/from the sensor control device 102 and/or the reader device 120. In the case of an exemplary BLUETOOTH®-enabled sensor control device 102 and/or reader device 120, a pairing mode may be entered into when the sensor control device 102 approaches the vehicle 1106. Upon pairing, the control module 1104 may be programmed and configured to automatically detect the presence of and establish communication with the sensor control device 102 and/or the reader device 120. For example, when the operator 1102 approaches or enters the vehicle 1106, the control module 1104 may automatically detect the presence of the sensor control device 102 and enable communication therebetween or with the reader device 120.

In some embodiments, the control module 1104 may be in communication with a vehicle user interface 1108 included in the vehicle 1106, such as an infotainment system, a touchscreen display, or an information display. In such embodiments, the control module 1104 may visually communicate with the operator 1102 via the vehicle user interface 1108 and may also be able to audibly communicate with the operator 1102 via the audio speakers included in the vehicle 1106. In other embodiments, however, the control module 1104 may be configured to communicate with the reader device 120 to be able to communicate with the operator 1102.

As illustrated, the control module 1104 may be or otherwise include a computer system 1110 configured and otherwise programmed to control various operations and/or systems of the vehicle 1106 based on real-time measured analyte levels of the operator 1102 as obtained by the sensor control device 102. Operation of the vehicle 1106 is controlled, disabled, or modified by either disabling one or more critical systems of the vehicle 1106 or by activating warning systems in the vehicle 1106. When the real-time measured analyte levels of the operator 1102 are within a predetermined safe range, then it may be considered safe for the operator 1102 to operate the vehicle 1106. When the real-time measured analyte levels of the operator 1102 fall outside the predetermined safe range or cross a predetermined threshold, however, the computer system 1110 may then be programmed to control, disable, or modify operation of the vehicle 1106.

In some embodiments, for example, the computer system 1110 may be configured to disable various critical vehicle systems when detected analyte levels of the operator 1102 fall outside of a predetermined range or otherwise cross a predetermined threshold, thus progressively and safely disabling operation of the vehicle when identifying the operator 1102 as impaired for safe operation of the vehicle 1106. Critical vehicle systems of the vehicle 1106 that may be disabled include the ignition system (e.g., energy switching/control system), the transmission system (or gear box), the fuel system, energy supply system (e.g., a battery, capacitor, conversion/reaction cell, etc.). When elevated or lowered (unsafe) analyte levels are detected, the computer system 1110 may prevent the critical vehicle systems from functioning or operating. Consequently, the operator 1102 will be unable to start or operate the vehicle 1106, thereby preventing the operator 1102 from placing themselves and/or others in danger.

In other embodiments, or in addition thereto, the computer system 1110 may be configured to activate various non-critical vehicle systems when detected analyte levels of the operator 1102 surpass or cross a predetermined threshold. Non-critical vehicle systems that may be activated include, for example, the vehicle horn, the vehicle lights, or an audible warning system installed in the vehicle 1106. In such embodiments, activation of the non-critical vehicle systems may alert law enforcement and others (e.g., operators of adjacent vehicles, bystanders, pedestrians, etc.) of an operator 1102 that may be driving in an impaired condition, thus allowing law enforcement to quickly address any issues related thereto and placing others on notice of a potentially dangerous situation.

In yet other embodiments, or in addition thereto, the computer system 1110 may be configured to automatically place a phone call to one or more emergency contacts when analyte levels of the operator 1102 fall outside of a predetermined safe operating range or otherwise cross a predetermined threshold. In such embodiments, the computer system 1110 may operate through the reader device 120 (e.g., a cellular phone) or a cellular or satellite communication system incorporated into the vehicle 1106 (e.g., OnStar®). In other embodiments, or in addition thereto, the computer system 1110 may be configured to automatically send a message (e.g., text or SMS message, email, etc.) to an emergency contact when analyte levels of the operator 1102 fall outside of a predetermined safe operating range or otherwise cross a predetermined threshold. Example emergency contacts include, but are not limited to, a spouse, a parent, medical personnel (e.g., a doctor), a hospital, 911, or any combination thereof.

In some embodiments, the system 1100 may further include one or more proximity sensors 1112 configured to detect the presence of the operator 1102 and, more particularly, the sensor control device 102. In such embodiments, the proximity sensor(s) 1112 may be configured to monitor the general area of the driver's seat 1114 within the vehicle 1106. If the sensor control device 102 is detected within the area of the driver's seat 1114 by the proximity sensor(s) 1112, that may provide a positive indication that the operator 1102 is in the driver's seat 1114 and potentially attempting to operate the vehicle 1106. In such cases, a signal may be sent to the control module 1104 alerting the computer system 1110 that the operator 1102 is in the vehicle 1106 and potentially attempting to operate the vehicle 1106. If the real-time measured analyte levels of the operator 1102 are within a predetermined safe range or below a predetermined level, then the computer system 1110 may allow the operator 1102 to operate the vehicle 1106. When the real-time measured analyte levels of the operator 1102 fall outside the predetermined safe range or cross a predetermined threshold, however, the computer system 1110 may control, disable, or modify operation of the vehicle 1106, as generally described above. As will be appreciated, the proximity sensor(s) 1112 may be advantageous in preventing operation of the vehicle 1106 only when the impaired operator 1102 is in the driver's seat 1114 and ready to operate the vehicle 1106. Consequently, a user wearing the sensor control device 102 is able to ride as a passenger in the vehicle 1106 in any state without affecting operation of the control module 1104 or the vehicle 1106.

In some embodiments, the control module 1104 may further include a vehicle status detection module 1116 configured to detect the current status of the vehicle 1106, including whether the vehicle 1106 is currently moving or is stationary. In addition, the vehicle status detection module 1116 may be configured to determine whether or not the motor in the vehicle 1106 is currently operating or is stopped. In one or more embodiments, the vehicle status detection module 1116 may provide a status signal to the control module 1104, and the control module 1104 can then use the status signal to determine what vehicle operations should be activated or disabled when the real-time measured analyte levels of the operator 1102 fall outside the predetermined safe range or cross a predetermined threshold. For example, when the status signal indicates that the vehicle 1106 is stationary, the control module 1104 can disable the vehicle fuel system, transmission system, ignition system, or any combination thereof. In contrast, when the status signal indicates that the vehicle 1106 is moving, the control module 1104 can activate the vehicle horn, flash the vehicle lights, or activate an audible warning to the operator 1102 and/or those around the operator 1102 that the operator 1102 is impaired.

In some embodiments, once the operator 1102 enters the vehicle 1106 or when the control module 1104 pairs with the sensor control device 102 and/or the reader device 120, an app may be launched on the reader device 120 or the vehicle user interface 1108, and a digital dashboard may appear on the reader device 120 and/or the vehicle user interface 1108 that depicts current analyte levels, trend, historical data, and projected analyte levels. If the current analyte levels fall outside of a predetermined safe operating range, however, the computer system 1110 may be programmed to disable one or more critical vehicle systems to prevent the operator 1102 from operating the vehicle 1106. In such embodiments, a visual or audible alert may be issued by the control module 1104 to inform the operator 1102 as to why the vehicle 1106 is not starting. More particularly, a visual alert (e.g., a written message) may be generated and displayed on the reader device 120 or the vehicle user interface 1108, or an audible alert (e.g., a vocal message) may be transmitted through the speakers in the reader device 120 or the vehicle 1106.

If not done automatically, the operator 1102 may be prompted to obtain a current analyte level upon pairing the sensor control device 102 with the control module 1104. In some cases, the vehicle 1106 may be prevented from being operated until a current analyte level is obtained. If the current analyte levels are within safe limits, the computer system 1110 may allow operation of the vehicle 1106. In some aspects, and unless done automatically, the control module 1104 may prompt the operator 1102 to obtain additional current analyte levels after operating the vehicle 1106 for a predetermined period of time (e.g., after 1 hour, 2 hours, 5 hours, etc.).

In some embodiments, the control module 1104 may be configured to issue visual or audible recommendations or coaching to the operator 1102 that may help bring measured analyte levels back into safe ranges. In such embodiments, such visual or audible recommendations may prompt the user to take some action that could result in bringing analyte levels back into safe ranges. Moreover, in some embodiments, the operator 1102 may be able to communicate with the control module 1104 verbally by issuing verbal responses or commands. This may prove advantageous in helping prevent distracted operation of the vehicle 1106.

In some embodiments, settings of the control module 1104 may be customized by the operator 1102 to allow the user to make informed decisions once unsafe analyte levels have been detected and a visual or audible alert has been issued by the control module 1104. More specifically, in at least one embodiment, the control module 1104 may include a bypass feature that the operator 1102 might enable to allow the operator 1102 to operate the vehicle 1106 even when unsafe analyte levels have been measured. In such embodiments, the operator 1102 may operate the vehicle 1106 by acknowledging that the operator 1102 might be operating the vehicle 1106 in an impaired or unsafe health state.

In some embodiments, the computer system 1110 may be configured or otherwise programmed to calculate a predicted timeline when analyte levels of the operator 1102 may depart from a predetermined safe range or otherwise cross a predetermined threshold. In such embodiments, the control module 1104 may be configured to issue visual or audible alerts to the operator 1102 indicating approximately how much time the operator 1102 has before unsafe analyte levels may be reached and a potential unsafe medical condition may ensue. Multiple alerts may be provided to indicate when the operator has specific time increments remaining before unsafe analyte levels are reached. For example, visual or audible alerts may be issued when unsafe analyte levels will be reached within an hour, within a half hour, within 10 minutes, within 5 minutes, within 1 minute, and any time increment therebetween. Furthermore, a visual or audible alert may be issued once the analyte levels of the operator reach an unsafe level or cross a predetermined threshold.

In some embodiments, if unsafe analyte levels are measured while the operator 1102 is operating the vehicle 1106, the control module 1104 may be configured to issue one or more alerts (visual or audible) warning the operator 1102 of the unsafe analyte levels. In some cases, the volume of the stereo in the vehicle 1106 may be automatically lowered to enable the operator 1102 to hear an audible alert. In such embodiments, the control module 1104 may be configured to suggest one or more corrective actions to the operator 1102. Example corrective actions include, but are not limited to, slowing and stopping the vehicle 1106, locating and driving to a nearby convenience store or pharmacy, and locating a nearby hospital or medical facility. If the vehicle 1106 is an autonomous vehicle, and the current analyte levels place the operator 1102 in potentially dangerous conditions, the control module 1104 may automatically direct the vehicle 1106 to a medical facility for treatment. Alternatively, or in addition thereto, the control module 1104 may progressively reduce or restrict the speed of the vehicle 1106 when unsafe analyte levels are detected, thus forcing the operator 1102 to come to a stop and remedy the issue before continuing to operate the vehicle 1106.

The system 1100 may be useful in several different scenarios to protect the operator 1102 and/or those around the operator 1102 while driving. In some applications, the system 1100 may be incorporated voluntarily by the operator to detect impairment in real-time. In other applications, the system 1100 may be required by the owner of the vehicle 1106 to detect impairment of the operator 1102. In such applications, the owner of the vehicle 1106 may be a transport or trucking company. In yet other applications, the system 1100 may be legally imposed on the operator 1102 to detect impairment.

Embodiments Disclosed Herein Include:

F. An analyte monitoring and vehicle control system that includes a sensor control device having a sensor that detects and monitors one or more analytes present within a body of an operator, and a control module in communication with the sensor control device and an electrical system of a vehicle, the control module including a computer system programmed to receive and process data provided by the sensor control device, wherein operation of the vehicle is controlled or disabled by the computer system when a real-time measured analyte level of the operator crosses a predetermined safe threshold.

G. A method that includes detecting and monitoring one or more analytes present within a body of an operator with a sensor control device having a sensor, receiving and processes data provided by the sensor control device with a control module in communication with the sensor control device and an electrical system of a vehicle; and controlling or disabling operation of the vehicle with a computer system of the control module when a real-time measured analyte level of the operator crosses a predetermined safe threshold.

Each of embodiments F and G may have one or more of the following additional elements in any combination: Element 1: wherein the sensor control device is coupled to the operator and the sensor is transcutaneously positioned beneath skin of the operator to detect and monitor the analytes present within a bodily fluid of the operator. Element 2: wherein the sensor control device comprises an ex vivo analyte sensor. Element 3: further comprising a reader device that receives the data from the sensor control device and transmits the data to the control module. Element 4: wherein the vehicle comprises a transportation vehicle selected from the group consisting of an automobile, an autonomous vehicle, a truck, a sport utility vehicle, an aircraft, a watercraft, a spacecraft, or any combination thereof. Element 5: wherein sensor control device pairs with the control module for communication upon the operator approaching the vehicle. Element 6: further comprising a vehicle user interface included in the vehicle and in communication with the control module. Element 7: wherein operation of the vehicle is disabled by disabling one or more critical systems of the vehicle, the critical systems being selected from the group consisting of an ignition system, a transmission system, a fuel system, and an energy supply system. Element 8: wherein operation of the vehicle is controlled by at least one of activating one or more non-critical systems of the vehicle, calling or sending a message to one or more emergency contacts, and progressively reducing a speed of the vehicle. Element 9: further comprising one or more proximity sensors installed on the vehicle to monitor an area of a driver's seat of the vehicle and detect a presence of the operator. Element 10: wherein the control module further includes a vehicle status detection module that detects the current status of the vehicle. Element 11: wherein the control module generates visual or audible alerts perceivable by the operator when the real-time measured analyte level of the operator falls outside of the predetermined safe threshold. Element 12: wherein the visual or audible alerts are generated at specific time increments before unsafe analyte levels are reached. Element 13: wherein the visual or audible alerts comprise one or more suggested corrective actions communicated to the operator. Element 14: wherein the control module includes a bypass feature allowing the operator to operate the vehicle when the real-time measured analyte level of the operator crosses the predetermined threshold.

Element 15: further comprising receiving the data from the sensor control device and transmitting the data to the control module with a reader device in communication with the sensor control device and the control module. Element 16: wherein disabling operation of the vehicle comprises disabling one or more critical systems of the vehicle, the critical systems being selected from the group consisting of an ignition system, a transmission system, a fuel system, and an energy supply system. Element 17: wherein controlling operation of the vehicle comprises at least one of activating one or more non-critical systems of the vehicle, calling or sending a message to one or more emergency contacts, and progressively reducing a speed of the vehicle. Element 18: further comprising monitoring an area of a driver's seat of the vehicle and detecting a presence of the operator with one or more proximity sensors installed on the vehicle. Element 19: further comprising detecting the current status of the vehicle with a vehicle status detection module included in the control module. Element 20: further comprising generating visual or audible alerts perceivable by the operator with the control module when the real-time measured analyte level of the operator crosses the predetermined threshold.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. An analyte sensor comprising:
a) a working electrode;
b) a glucose-responsive active area disposed upon a surface of the working electrode, the glucose-responsive active area comprising a glucose-responsive active enzyme capable of generating a first signal at the working electrode proportional to a glucose concentration;
c) an ethanol-responsive active area comprising:
i) a first active area disposed directly upon the surface of the working electrode spaced apart from the glucose-responsive active area, the first active area comprising xanthine oxidase and an electron transfer agent, in amounts sufficient to react with acetaldehyde to generate a second signal at the working electrode proportional to an alcohol concentration; and
ii) a second active area isolated from the working electrode, the second active area comprising glucose oxidase and catalase in amounts sufficient to form acetaldehyde upon exposure to ethanol;
d) a first membrane permeable to acetaldehyde disposed upon the first active area; and
e) a second membrane permeable to glucose and ethanol disposed upon the glucose-responsive active area and the second active area,
wherein the second active area is disposed directly upon the first membrane, and
wherein the sensor is configured to be partially inserted into a user's skin.

2. The analyte sensor of claim 1, wherein the first and second membranes comprise a polyvinylpyridine, a polyvinylimidazole, or any copolymer thereof.

3. The analyte sensor of claim 1, wherein the first membrane comprises polyvinylpyridine and the second membrane comprises polyvinylpyridine-co-styrene.

4. The analyte sensor of claim 1, wherein the xanthine oxidase is covalently bound to a first polymer, and the glucose oxidase is covalently bound to a second polymer.

5. The analyte sensor of claim 4, wherein the electron transfer agent is covalently bound to the first polymer.

6. The analyte sensor of claim 5, wherein the electron transfer agent comprises an osmium complex.

7. The analyte sensor of claim 1, wherein the first active area further comprises catalase.

8. The analyte sensor of claim 1, wherein the glucose-responsive enzyme is glucose oxidase or glucose dehydrogenase.

9. The analyte sensor of claim 1, further comprising:

a control module in communication with the analyte sensor and an electrical system of a vehicle, the control module including a computer system programmed to receive and process data provided by the analyte sensor, wherein operation of the vehicle is controlled or disabled by the computer system when a real-time measured analyte level of the operator crosses a predetermined safe threshold.

10. The analyte sensor of claim 1, wherein the glucose-responsive active area further comprises a second electron transfer agent.

11. A method comprising:

exposing an analyte sensor to a body fluid comprising at least one of glucose and ethanol, the analyte sensor comprising:
- a) a working electrode;
- b) a glucose-responsive active area disposed upon a surface of the working electrode, the glucose-responsive active area comprising a glucose-responsive active enzyme capable of generating a first signal at the working electrode proportional to a glucose concentration;
- c) an ethanol-responsive active area comprising:
  - i) a first active area disposed directly upon the surface of the working electrode spaced apart from the glucose-responsive active area, the first active area comprising xanthine oxidase and an electron transfer agent, in amounts sufficient to react with acetaldehyde to generate a second signal at the working electrode proportional to an alcohol concentration; and
  - ii) a second active area isolated from the working electrode, the second active area comprising glucose oxidase and catalase in amounts sufficient to form acetaldehyde upon exposure to ethanol;
- d) a first membrane permeable to acetaldehyde disposed upon the first active area;
- e) a second membrane permeable to glucose and ethanol disposed upon the glucose-responsive active area and the second active area, and detecting a first signal proportional to a glucose concentration and the second signal proportional to an ethanol concentration, wherein the second active area is disposed directly upon the first membrane, and wherein the sensor is configured to be partially inserted into a user's skin.

12. The method of claim 11, wherein the glucose-responsive active area further comprises a second electron transfer agent.

* * * * *